(12) United States Patent
Pera et al.

(10) Patent No.: US 8,673,637 B2
(45) Date of Patent: Mar. 18, 2014

(54) HUMAN MULTIPOTENT GERM LINE STEM CELLS EXPRESSING A GERM LINE MARKER AND A PLURIPOTENCY MARKER PRODUCED BY CO-CULTURE OF TESTICULAR TISSUE

(75) Inventors: Renee Reijo Pera, Palo Alto, CA (US); Paul J. Turek, Palo Alto, CA (US); Juanito Meneses, Palo Alto, CA (US); Nina Kossack, Münster (DE)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 514 days.

(21) Appl. No.: 12/589,179

(22) Filed: Oct. 16, 2009

(65) Prior Publication Data

US 2010/0267134 A1 Oct. 21, 2010

Related U.S. Application Data

(60) Provisional application No. 61/136,948, filed on Oct. 16, 2008.

(51) Int. Cl.
*C12N 15/00* (2006.01)
*C12N 15/02* (2006.01)
*C12N 5/00* (2006.01)
*C12N 5/076* (2010.01)
*C12N 5/071* (2010.01)

(52) U.S. Cl.
CPC .............. *C12N 5/061* (2013.01); *C12N 5/0068* (2013.01); *C12N 5/0608* (2013.01); *C12N 5/0018* (2013.01)
USPC ........... 435/377; 435/373; 435/375; 435/378; 435/387; 435/366

(58) Field of Classification Search
CPC .... C12N 5/061; C12N 5/0068; C12N 5/0608; C12N 5/0018
See application file for complete search history.

(56) References Cited

PUBLICATIONS

Nagano et al. Long-term survival of human spermatogonial stem cells in mouse testes. Fertil. Sterility, 2002, vol. 78, pp. 1225-1233.*
Lee et al. Isolation of male germ stem cell-like cells from testicular tissue of non-obstructive azoospermic patients and differentiation into haploid male germ cells in vitro Human Reprod., 2006, vol. 21, pp. 471-476.*
Gupta et al. Human CD341 Bone Marrow Cells Regulate Stromal Production of Interleukin-6 and Granulocyte Colony-Stimulating Factor and Increase the Colony-Stimulating Activity of Stroma Blood, 1998, vol. 91, pp. 3724-3733.*
Lu et al. Three-dimensional co-culture of rat hepatocyte spheroids and NIH/3T3 fibroblasts enhances hepatocyte functional maintenance ActaBiomaterialia, 2005, vol. 1, pp. 399-410.*
Silva et al. Therapeutic Potential of Stem Cells in Reproductive Medicine. Serono Symposia International Foundation, Mar. 31-Apr. 1, 2006, p. 6.*

* cited by examiner

*Primary Examiner* — Deborah Crouch
(74) *Attorney, Agent, or Firm* — Mark G Lappin

(57) ABSTRACT

A method of in vitro maturation of adult human germ line cells in an artificial biological environment, which entails:
  a) isolating human spermatogonial stem cells (SSCs), and optionally purifying the same; and
  b) co-culturing the isolated and optionally purified SSCs with a suitably adjusted Sertoli cell environment to obtain haploid germ cells.

34 Claims, 14 Drawing Sheets

SRY

HOLLOW-FIBER CAPILLARY CULTURE

HUMAN MULTIPOTENT GERM LINE STEM CELLS EXPRESSING A GERM LINE MARKER AND A PLURIPOTENCY MARKER PRODUCED BY CO-CULTURE OF TESTICULAR TISSUE

This invention was made with Government support under contract HD047721 awarded by the National Institutes of Health. The Government has certain rights in this invention.

BACKGROUND OF THE INVENTION

1. Field of the Invention

The present invention provides a method of isolation, characterization and artificial differentiation of in vitro adult human germ cells.

2. Description of the Background

Over the years, culture conditions for mouse spermatogonial stem cells (SSCs) have been established, facilitating the characterization of these cells and factors involved in self-renewal and differentiation. Nonetheless, several lines of evidence suggested that the ability to derive pluripotent germ cell lines was restricted to the earliest stages of development (to PGCs) and that pluripotency of germ cells was not maintained postnatally. However, recent results from mice have challenged this assumption. The pluripotency of mouse spermatogonia-derived stem cells termed mGSCs (multipotent germline stem cells), maGSCs (multipotent adult germline stem cells) or MACS (multipotent adult spermatogonial-derived stem cells) has been demonstrated by several criteria including ability to spontaneously differentiate into derivatives of the three primary germ layers and to contribute to chimeras. Notably, elegant studies in mice have resulted in the identification of the progenitor population and delineation of the time course of acquisition of pluripotency.

Since publication of these mice studies, research has been directed toward duplicating these findings in vitro with human spermatogonial stem cells. If reproducible in humans, these findings would identify the testicle as a source of multipotent or even pluripotent stem cells that might be used for patient-specific, non-embryo derived, stem cell-based therapy in the future. It would also suggest the possibility of differentiating testis stem cells to more mature, haploid forms and even to sperm.

Germ cell maturation has proven to be a difficult task in the laboratory. This has precluded the in vitro maturation of early human germ cells to mature sperm. The development of mature sperm would provide new therapies for men who have been rendered sterile for various reasons, including cancer treatment. It would also provide an in vitro construct to study the biology of spermatogenesis and the effects of reproductive toxins and drugs in sperm production. Thus, a need for a method of maturing early human germ cells to mature sperm continues to exist.

SUMMARY OF THE INVENTION

Accordingly, it is an object of the present invention to provide a method for the isolation and characterization of early germ live stem cells.

It is also an object of the present invention to provide a method of in vitro maturation of human adult testis stem cell to haploid germ cells.

It is also an object of the present invention to provide a biological environment that supports germ cell maturation to haploid cells.

DETAILED DESCRIPTION OF THE PREFERRED EMBODIMENTS

Figure 1A:
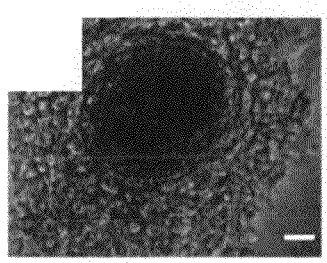
FIG. 1 illustrates morphological analysis for the expression of both pluripotency and germ cell specific markers.

Certain terms used in the present specification are as defined as noted below.

Term Definitions

Sertoli cells: Any of the elongated striated cells in the seminiferous tubules of the testes to which the spermatids become attached and from which they appear to derive nourishment.

Spermatid: Any of the haploid cells formed by meiosis in a male organism that develops into spermatozoa with further division.

Spermatogonium: An unspecialized diploid early germ cell with the testis seminiferous tubules which can undergo mitosis and meiosis to give rise to a sperm cell.

Spermatogonial stem cells (hSSCs or SSCs): An early germ cell with multipotent or pluripotent potential that can be reprogrammed to have embryonic stem cell-like properties or differentiated down the germ cell lineage to sperm.

Early testis germ cell: An early germ cell of the spermatogonial stem cell type or closely related type that may or may not have multipotent or pluripotent properties.

Isolated and/or artificial biological environment. A man-made environment that is capable of supporting cultured cells in a viable manner using suitable condition. Examples are monolayer cultures hollow-fiber capillary tube cultures and transwell insert cultures, which are all isolated and artificial. Conditions used therein are "suitably adjusted," meaning adjusted to obtain the most viable conditions to support cell growth, which includes nutrient media, temperature, etc.

Materials and Methods

Patient Information

Testis biopsies are routinely obtained for the diagnosis of male fertility through the clinical practice of Paul Turek and can be used for research following informed consent. In this study, nineteen patient samples were obtained and one hMGSC line (termed NK7) was generated from an individual who was diagnosed with azoospermia due to acquired reproductive tract obstruction from trauma (obstructive azoospermia). This individual donor presented with normal hormone values (FSH 5 IUII, LH 2.9 IUII, T 408 ngldl and prolactin 13 ng/ml), normal karyotype in a blood sample, and no detectable Y chromosome microdeletions. Histologically, testis sections showed normal spermatogenesis (Supplemental data (A)). See FIG. 7.

Collection of Tissue

Approximately 30-50 mg sections of testis tissue were excised and placed into MEM-a medium (Invitrogen, Inc; Carlsbad, Calif.). Tissue was mechanically dissected and dissociated via a two-step enzymatic incubation process: First, tissues were incubated for 30 min at 37° C. in MEM-a media containing 10 mg/ml collagenase (Invitrogen, Inc).

Spermatogenic tubules, tissues and cells were then centrifuged, 5 min, 1000 rpm and resuspended in 2 ml of Hank's balanced salt solution (Invitrogen, Inc) containing 2.2 mg/ml DNAse I (Roche Applied Science, Inc; Indianapolis, Ind.) and 4 mg/ml trypsin (Invitrogen, Inc) and incubated for 10 min at 37° C. Then, 2.5 volumes MEM-a medium containing 10% fetal bovine serum (FBS) (Invitrogen, Inc) were added to the cell suspension; cells were washed three times with phosphate buffered saline solution (PBS; Invitrogen, Inc) and resuspended in MEM-a medium supplemented with 10% FBS and 1% PedStrep.

Isolation of Spermatogonial Stem Cells

Initially, we explored several methods to isolate and propagate human spermatogonial stem cells. In one approach, we treated testicular biopsy cells as described above and simply transferred the sample in total directly to gelatin-coated tissue culture plates. In a second approach, we attempted to enrich for the spermatogonial stem cell population via magnetic activated cell sorting (MACS) for the GDNF family receptor-alpha-1 (GFR-a1). To induce the propagation of ESC-like cells from testis biopsies, we further tested alternatives of plating testicular cells directly in hESC media without MEFs, plating cells in hESC media directly onto MEFs, and plating cells in hESC media with subsequent transfer to MEFs after 8 days; hESC media is as described.

Transfer and Culture Conditions of Spermatogonial Stem Cell Colonies

Two days post-plating, most testicular cells were attached to the growing surface and the media was changed. After approximately one week several small colonies were observed on top of the monolayer of testicular cells. To propagate these colonies under hESC conditions, they were manually transferred onto mouse embryonic fibroblasts (MEFs) and cultured in knockout DMEM, (Invitrogen, Inc) supplemented with 20% FBS, 1 mM L-glutamine (Invitrogen, Inc), 0.1 mM nonessential amino acids (Invitrogen, Inc), 0.1 mM P-mercaptoethanol (Chemicon International, Billerica, Mass.) and 10 ng/ml recombinant human basic fibroblast growth factor (bFGF) (R&D Systems; Minneapolis, Minn.) referred to hereafter as KSR media. To inhibit putative stem cells from differentiating, after five days, cells were passaged onto ultra-low attachment dishes.

Manual passaging was performed for the 2 initial passages and was followed by enzymatic digestion using a combination of 0.01 mg/ml collagenase (100 Units/ml, 37° C., 5 min) (Invitrogen, Inc) and trypsin (0.25% trypsinEDTA, 37 T, 5 min) for later passages. Prior to transfer onto ultra-low attachment dishes (Corning, Inc; Corning, N.Y.), cells were washed three times in KSR media. After 2 days, putative stem cells were plated onto MEFs.

RNA Isolation and cDNA Amplification

Total RNA was extracted with the RNeasy Mini Kit (Qiagen; Valencia, Calif.). cDNA was generated from 100 ng of RNA isolated from hMGSCs cultured on MEFs at passage 2 and passage 7, from hMGSCs cultured on human testicular stromal cells and from testicular tissue (Clontech; Mountain View, Calif.) using Superscript™ 111 Reverse Transcriptase (Invitrogen, Inc). Subsequent PCR analysis was performed with Platinum Taq DNA Polymerase (Invitrogen, Inc) using 10 ng of cDNA as template to analyze expression of the genes: OCT-4, SOX-2, NANOG, STELLAR, GDF3, PUMILIOI (PUMI), PUMILIO2 (PUM2), DAZL, VASA, SCP1, SCP3, MLHI, BOULE and TEKTl with primers as shown (Supplementary Table 1) and cycling: 94° C. for 1 min followed by 40 cycles at 94 T, 30 sec; 60° C., 30 sec; 72 T, 30 sec.

Immunofluorescence and Alkaline Phosphatase Staining of Undifferentiated Colonies Alkaline phosphatase staining was accomplished via the Vector Red Alkaline Phosphatase Substrate Kit I (Vector Laboratories, Inc; Burlingame, Calif.) with H9 hESCs as a positive control. For immunofluorescence, undifferentiated cells were cultured on MEFs and were fixed in 4% paraformaldehyde in PBS (pH 7.4), 20 min. Cells were washed twice with PBS/0.1% Tween-20 to remove residual fixative and incubated in 1% Triton X in PBS, 30 min, prior to blocking in 4% normal goat serum in PBS (Jackson ImmunoResearch Laboratories; West Grove, Pa.) for 30 min followed by incubation with antibody solution overnight at 4° C. Primary antibodies included: OCT-4 (1:200, Santa Cruz Biotechnology; Santa Cruz, Calif.), SOX2 (1:200, Chemicon; Billerica, Mass.), SSEA-4 (1:200, Chemicon; Billerica, Mass.), TRAI-81 (1:200, Chemicon; Billerica, Mass.) and DAZL (1:100 as described). The following day, cells were washed twice with PBS/0.I% Tween-20, 5 min, and incubated with appropriate secondary antibody (1:200, Invitrogen) in PBS. After two washes with PBS+0.1% Tween-20, 5 min, cells were mounted with anti-fade mounting media or DAPIPBS and viewed on a Leica DMIL microscope or on a Zeiss LSM 5 10 Confocal Laser Scanning Microscope equipped for two-photon excitation.

Spectral Karyotyping (SKY)

Growing colonies were incubated with 0.1 ug/ml colcemid (Gibco) at 37° C. overnight. Cells were enzymatically detached as described above and resuspended in KSR medium. To achieve single cell suspension, cells were pelleted at 1,000 rpm for 5 min, resuspended in 0.25% Trypsin:EDTA (Gibco, Inc) and incubated at 3 TC, 5 min. KSR was added to inactivate the trypsin; cells were pelleted and resuspended in 0.4% sodium citrate and 0.4% KCl at a 1:1 ratio and incubated at 37° C. for 15 min. An equal volume of Carnoy's solution (3:1 ratio of methanol to acetic acid) was added followed by incubation at room temperature, 5 min, to fix cells (this step was repeated twice with fresh fixative).

Finally, pellets were resuspended in a small volume of fixative and transferred to microscope slides. SKY analysis was performed using SkyPaint Human H-10 according to manufacturer's instructions (Applied Spectral Imaging, Inc., Vista, Calif.) and visualized on a Leica DMR Microscope with an Applied Spectral Imaging unit SD-301-VDS.

STRNNTR Analysis

Genomic DNA was extracted from hMGSCs via the QIAamp DNA Mini system (Qiagen) and from tissue donor blood via the QIAamp DNA Blood Maxi Kit (Qiagen).

Genomic DNA from the hESC line H9 was used as a negative control. 10 pl of genomic DNA at a concentration of 2.5 ng/pl were submitted for analysis via AmpFtSTRBIdentifilerTMPCR Amplification (Applied Biosystems; Foster City, Calif.). Fifteen tetranucleotide repeat loci and the amelogenin gender determining marker were analyzed.

Bisulphite Sequencing Analysis hMGSCs were cultured in feeder free conditions for two days, collected, washed with PBS, quick-frozen on dry ice and stored at −80° C. H9 hESCs, sperm and whole blood genomic DNA served as controls. Genomic DNA was extracted via the QIAamp DNA Mini system. Conversion of unmethylated cytosines was performed via the Methyl Easy™ Xceed Rapid DNA Bisulphite Modification Kit (Human Genetic Signatures; Sydney, Australia). 0.5-1 ug of genomic DNA were used for bisulphite treatment, resulting in a final converted DNA concentration of 15-20 nglul. 4 pl of product was amplified. Seminested PCR was performed via 2 rounds: 1) 94 T, 10 min, followed by 30 cycles of 94° C., 45 sec; 61° C., 45 sec; 72° C., 1 min and a final extension step of 72° C., 10 min; 2) 35 cycles (same conditions but second set of primers). Primers were human specific H19 forward 5'-AGGTGTTTTAGTTTTATGGATGATGG-3', H19 forward 2 5'-TGTATAGTATATGGGTATTTTTGGAGGTTT-3' and HI9 reverse 5'-TCCTATAAATATCCTATTC-CCAAATAACC-3' as described in Kerjean et al. PCR products were gel purified and cloned into a TOPOB Vector (Invitrogen, Inc). In addition, the DNA methylation profile of the 5'-flanking region of the human OCT4 gene was analyzed. The region that was investigated was between −2564 bp to +153 bp from the transcription start site (TSS) and contains the proximal enhancer (PE), the distal enhancer (DE) and the proximal promoter (PP) as indicated in FIG. 3. Primer pairs OCT4-2F/2R, OCT4-3F/3R, OCT4-5F1R and OCT4-9F/R and PCR conditions were used as described in Deb-Rinker er al.

Telomerase Activity

Telomerase activity was analyzed in duplicates using the TRAPEZE@ ELISA Telomerase Detection Kit (Chemicon). Cells were grown, feeder-free, for 2 days, collected, washed with PBS and subsequently quick-frozen on dry ice. The hESC line HSF8 (XY) was used as a positive control. Cells were lysed in 1×CHAPS lysis buffer and protein concentration was determined via BCA assay (Pierce Biotechnology, Inc; Rockford, Ill.).

Sample extracts were diluted 1:100 with 1×CHAPS lysis buffer, using approximately 3 ng protein per extract for the TRAPEZE ELISA Telomerase Detection Kit Assay. Amount of product was determined using a Multiscan EX automatic microplate reader (Thermo, Inc; Milford, Mass.). Absorbance was measured at 450 nm and 620 nm and telomerase activity was determined: Absorbance=A450-'4620. Heat-treated extracts (99° C. for 20 min) were analyzed in parallel as a negative control.

Differentiation of hMGSCs

To induce embryoid body (EB) formation, hMGSCs were dissociated with trypsin, neutralized with KSR media, and washed 3 times with differentiation media (Knockout DMEM supplemented with 20% FBS, 1 mM L-glutamine, 0.1 mM nonessential amino acids and 0.1 mM !3-mercaptoethanol) prior to transfer onto ultra low attachment dishes.

One third of the resulting EB suspension was collected on days 0, 3, 7, 11, 14 and 21 to determine differentiation status at these time points. RNA was isolated via the Pico Pure RNA isolation Kit (Arcturus, Inc; Mountain View, Calif.), transcribed into cDNA via the WT-Ovation RNA Amplification System (NuGEN Technologies; San Carlos, Calif.) and analyzed. H9 hESCs were used as a positive control for each differentiation experiment.

Real-time PCR using Taqman Gene Expression Assays (Applied Biosystems) was performed to determine the expression levels of OCT-4 (HsO1895061-ul), MSIl (Hs 00159291-ml), GATA4 (Hs 00171403-ml) and NCAM (HsOO169851-ml) using 20 ug of cDNA per reaction. Expression values were normalized for GAPDH and calculated as previously described [35]. KDR expression was analyzed using SYBR green (Applied Biosystems) RT-PCR. All experiments included controls without any cDNA template for each primer set.

For teratoma assays, cells were cultured under feeder free conditions for 2 days, then incubated in 0.25% trypsin1 EDTA for 5 min at 37 T and transferred to KSR media supplemented with 20% FBS and 10 ng/pl bFGF. After two washes, cells were resuspended in 1 ml of KSR and aliquoted into 2×0.5 ml tubes. Cell pellets were collected to prepare two grafts. PHA (phytohemagglutinin) was added to a final concentration of 0.2 rng/ml, cells were pelleted by centrifugation at 10 000 g for 1 min and the cell pellet was incubated for 5 min at room temperature. The two cell pellets were transferred into 0.4 pM Millicell-CM inserts (Millipore, Inc; Temecula, Calif.) in a 2 cm dish containing KSR media. Grafts were incubated overnight at 37° C. and implanted under the kidney capsule of a female SCID recipient mouse in accordance with a known NIH procedure. Grafts were harvested and fixed with 4% paraformaldehyde 8 weeks post-transplantation. Fixed tissue was paraffin embedded, sectioned and stained with hematoxylin and eosin.

To investigate if teratoma formation would be more efficient if larger cell numbers and/or support cells were transplanted, approximately 10,000 hMGSCs were combined with 1 million irradiated MEFs. After two washes, cells were resuspended in 1 ml of KSR media and aliquoted into 2×0.5 ml tubes. Cell pellets were collected to prepare two grafts and transplantation of the grafts was performed as described above. 1 million irradiated MEF cells were used to prepare two grafts, which served as a negative control.

To analyze origin of cells in grafts, genomic DNA was isolated using the QIAarnp DNA Mini system (Qiagen, Inc). 60 ng DNA was used as a template to detect human SRY (Sex Determining Region Y). A 350 bp fragment was amplified using primers SRY forward 5'-CGCATTCATCGTGTG-GTCTCG-3' and SRY reverse 5'-AGCTGGTGCTCCAT-TCTTGAG-3'. PCR was performed as follows: 94° C. for 1 min and 35 cycles of 94° C. for 1 min, 58° C. for 45 sec and 72° C. for 45 sec. Resulting DNA fragments were separated by gel electrophoresis. Samples included NK7 hMGSC grafts, NK7 hMGSC genomic DNA, human sperm genomic DNA, and genomic DNA isolated from the tail tip of a female SCID mouse.

Immunofluorescence Staining of Differentiated hMGSCs

To assess differentiation, hMGSCs were differentiated in EBs for 7 days; then EBs were plated onto gelatin-coated dishes approximately 12 hrs prior to immunofluorescence analysis. Markers used were the endoderm marker, von Willebrand factor (VWN), the mesoderm marker, cardiac fetal actin (ACTC), and the ectoderm marker, nestin (NES).

Prior to staining, cells were fixed with 4% PFA for 15 min, fixed cells were then washed with PBS and blocked in PBS-BT, 30 min. Cells were incubated for 90 min with primary antibodies for VWN (1:400, Abcam, Cambridge, Mass.) and ACTC (1:10, Research Diagnostics Inc.; Concord, Mass.) and overnight at 4° C. with the NES primary antibody (1:100; Abcam; Cambridge, Mass.). Following incubation, cells were washed with 0.3% bovine serum albumin (Sigma-Aldrich; St Louis, Mo.) plus 0.1% Triton X-100 (Sigma-Aldrich) in PBS (PBS-BT) for 5 min, stained with the corresponding secondary antibody at a 1:200 dilution for 1 hr, washed three times in PBS-BT, counterstained with DAPI and viewed on a Leica DMIL microscope.

Immunofluorescence Staining Following Induced Neural Differentiation

NK7 hMGSCs were plated onto gelatin and were cultured until 80% confluency was achieved. Subsequently, KSR media was replaced with DMEMIF12+Glutamax media (Invitrogen, Inc.) supplemented with N-2 (Invitrogen) for 2 weeks. After 2 weeks in culture, the media was then changed to Neurobasal Medium (Invitrogen) supplemented with B-27 (Invitrogen) for 4 weeks. Subsequently the expression of ectodermal specific markers such as NES, microtubule-associated protein 2 (MAP2) and beta-tubulin 111 (TUB 111) was analyzed by immunofluorescence staining. NES primary antibody was used at a dilutio—of 1:100 (Abeam; Cambridge, Mass.), MAP2 (Chemicon) at 1:200 and TUB I11 (Covance, Berkeley, Calif.) at 1:750.

Results

Isolation of hMGSCs From Human Testis Biopsies

In initial attempts to isolate hMGSCs, we obtained testis biopsies and generated cell suspensions by enzymatic digestion. We then sought to enrich for the spermatogonial stem cell population by MACS (Magnetic Affinity Cell Sorting) with the cell surface marker, GFR-a (the receptor for GDNF (glial cell line-derived neurotrophic factor)).

GFR-a had previously been reported to localize to a subset of type A spermatogonia in mice [36]. Isolated cells were cultured on gelatin coated dishes in MEM-n medium.

However, although the resulting cells were capable of being propagated in vitro, they had an elongated spindle-shaped appearance (similar to fibroblasts, distinctly different from hESCs, and lacked characteristic expression of cell surface markers of pluripotent cells. Thus, we explored alternative methods to induce the propagation of hESC-like cells from testis biopsies: 1) Culture of testicular cells in hESC media post-biopsy digestion, 2) culture of testicular cells in hESC media for 8 days post-digestion, with subsequent transfer onto MEFs, and 3) transfer directly onto MEFs in hESC media. We noted that all three of these approaches, in contrast to MACS-affinity separation, resulted in the formation of colonies. However, these colonies could not be successfully propagated in vitro; with passaging via trypsin digestion, the cultures would progressively become devoid of stem cell-like cell colonies. Thus, in 17 of 17 biopsies subjected to these protocols, no hMGSC line was derived. In contrast, as described below, by manual passaging we succeeded in the derivation of 2 hMGSC lines (although 1 patient withdrew from the study and materials were discarded in that case).

Figure 1B:
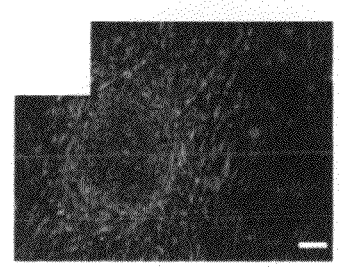
Figure 1C:
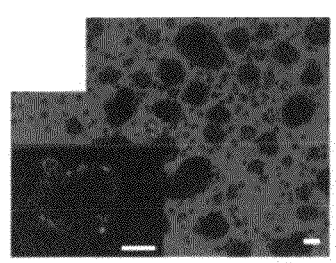

As an alternative, manual passaging of colonies was explored. Following enzymatic dmociation of the testis biopsy, after approximately 7-10 days of culture, very small colonies started to grow on top of the monolayer of testicular cells; these colonies were manually transferred onto MEFs and cultured under hESC conditions (FIGS. 1A, B). These cells, which we have termed human multipotent germ line stem cells (hMGSCs), have been propagated for approximately 17 passages in vitro; the current line is designated "NK7." The putative NK7 hMGSCs were passaged once every week and have maintained the ability to form colonies with characteristic hESC morphology for more than 20 passages. However, although the cells in the middle of the colonies have a distinctive hESC-like appearance, some of the cells at the periphery appear to differentiate and acquire a spindle-shaped morphology suggesting the need to optimize media and/or culture and derivation conditions (FIG. 1B). In suspension, NK7 cells continued to divide and formed EB (embryoid-body)-like structures (FIG. 1C).

Gene Expression Analysis

Figure 1D:
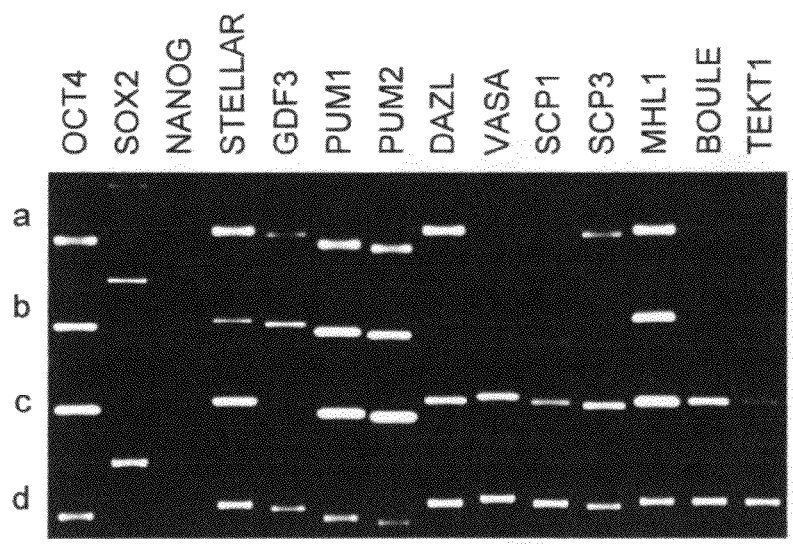

Reverse transcriptase-polymerase chain reaction (RT-PCR) was performed to analyze the expression of a subset of pluripotency markers as well as germ cell specific genes in the isolated hMGSCs at passage 2 and 7 (FIG. 1D a,b) relative to a normal human testis sample (FIG. 1D d). Results demonstrated that the hMGSCs passage 2 and 7 which were grown on MEFs express a subset of those genes expressed in the testis, as shown in FIG. 1D, that include the pluripotency markers OCT-4 (octamer-binding transcription factor-4) and SOX2 (SRY-box 2). NANOG expression, however, could not be detected in either the isolated hMGSCs or the testis sample. Apart from that, expression of the hESC- and germ cell-enriched genes, STELLAR (STELLA-related), GDF3 (growth and differentiation factor 3), PUM1 (PUMILIO 1) and PUM2 (PUMILIO 2) was observed. In addition, the hMGSCs expressed the germ cell-specific gene DAZL (Deleted in AZoospermia-Like), as well as, SCP3 (Syntaptonemal Complex Protein 3) and MLH1 (Mut-L Homolog 1). In contrast, expression of the markers, VASA and SCP1 was not detected, nor was the expression of the two developmentally-late germ cell markers BOULE and TEKT1 (FIG. 1D). Notably, the culture of NK7 cells on human testicular stromal cells induced the expression of later germ cell markers including BOULE and TEKT1 and led to a loss of SOX2 expression (FIG. 1D, c). We, therefore, concluded that NK7 cells lose the expression of later germ cell markers if cultured under human ESC conditions and regain the expression of pluripotency genes such as SOX2 if cultured on MEFs in human ESC conditions.

Figure 1E:
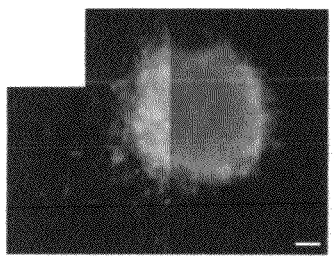
Figure 1F:
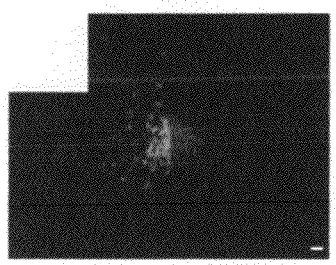
Figure 1G:
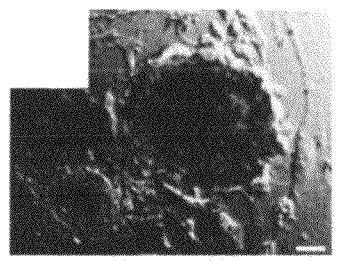
Figure 1H:
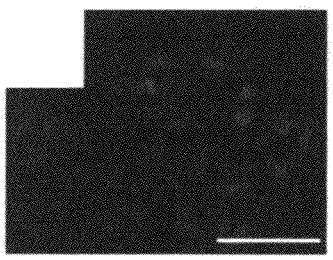
Figure 1I:
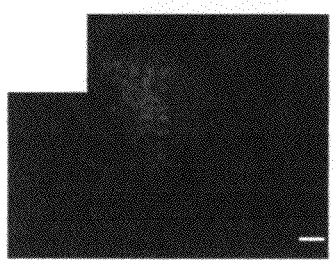
Figure 1J:
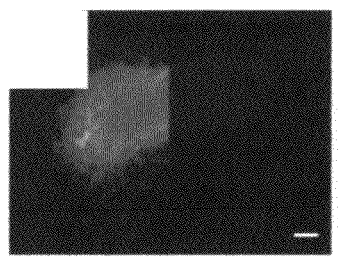

Our next aim was to examine the expression of pluripotency markers in hMGSCs by immunofluorescence (FIG. 1E-J). Putative hMGSCs were shown to express the human pluripotency markers SSEA4 (Stage Specific Embryonic Antigen 4; FIG. 1E), TRA1-81 (keratin sulfate-related antigens; FIG. 1F), OCT-4 (FIG. 1H) and SOX2 (FIG. 1I). In addition, the hMGSCs also stained positive for the early germ cell and hESC marker, TNAP (FIG. 1G), as well as the germ cell lineage marker, DAZL (FIG. 1J). Negative controls for all experiments demonstrated that antibodies were specific, as expected.

Spectral Karyotype

Figure 2A:
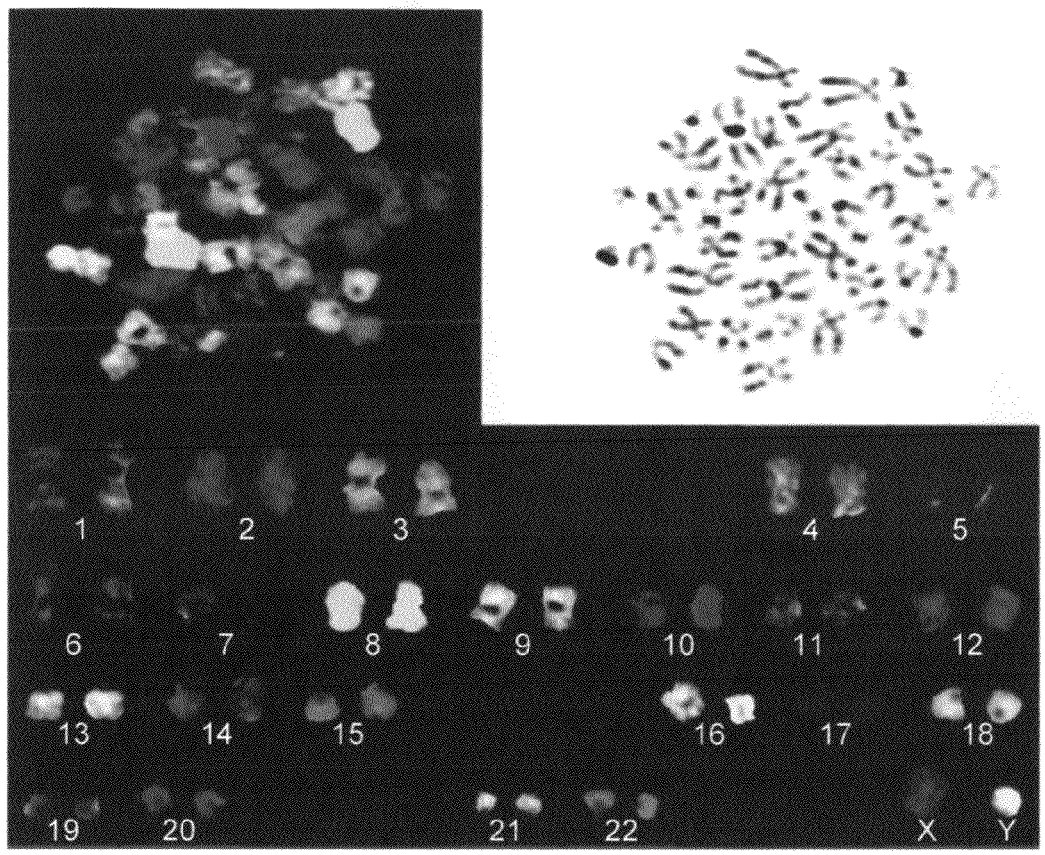
FIG. 2 illustrates that hMGSCs exhibit a normal karotype and express telomerase.

In order to determine the karyotype of the derived NK7 hMGSC line, SKY analysis was performed. Results demonstrated that the NK7 hMGSC line has a normal karyotype (46, XY) and no Y chromosome microdeletions. No indications of other cytogenetic abnormalities were detected (FIG. 2A). This indicated that the derived cell line was karyotypically identical to the patient's somatic cells, at this level of analysis.

STRNNTR Analysis

Short tandem repeat (STR)/variable number of tandem repeat (VNTR) analysis was performed to determine the origin of the NK7 hMGSCs. Samples analyzed were genomic DNA isolated from NK7 hMGSCs, genomic DNA from the tissue donor's blood sample and genomic DNA from H9 hESCs. The results (Table 1) demonstrate that the number of short tandem repeats on both alleles of the 15 loci that were analyzed is identical in NK7 hMGSCs and the tissue donor's blood sample. The probability that two randomly selected individuals would have an identical genotype at these 15 loci is minuscule ($5.01 \times 10$." [37]). Although H9 cells have the same number of short tandem repeats as the NK7 hMGSCs on both alleles of the HUMTHO1 locus and on one allele of the D16S539, D18S51 and D5S818 locus, the number of short tandem repeats at all other examined loci differed between H9 hESCs and the NK7 hMGSC line.

Telomerase Activity and Methylation of the HI9 DMR and the OCT-4 Promoter Region Telomerase activity is indicative of pluripotent stem cells. We examined telomerase activity of the hMGSCs at passage 6 and passage 8 relative to the human XY-bearing ESC line HSF8, as a positive control. As expected, hESCs exhibited a very high telomerase activity with little or no residual activity in the heat-inactivated control.

Figure 2B:
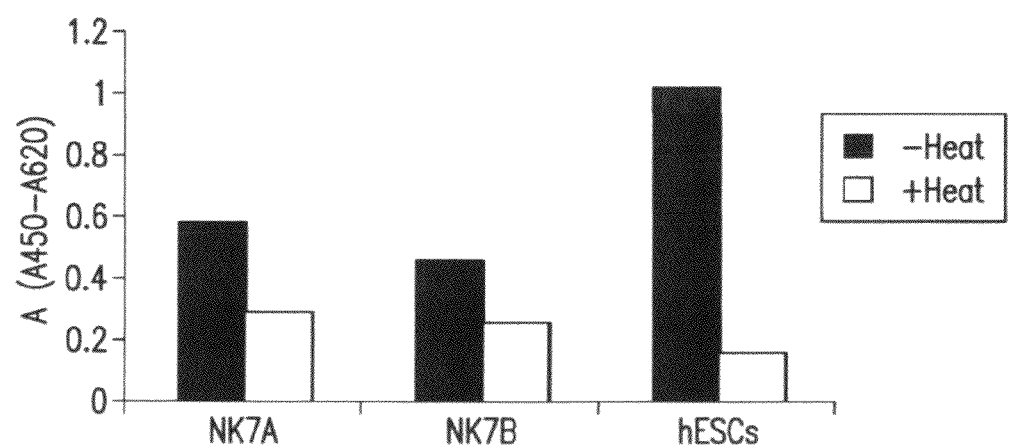

Telomerase activity was also detected in the two hMGSC extracts with the level of telomerase activity slightly reduced in cells which had been cultured for 8 passages relative to those cultured for 6 passages (FIG. 2B).

Bisulfite Sequencing

Figure 3A:
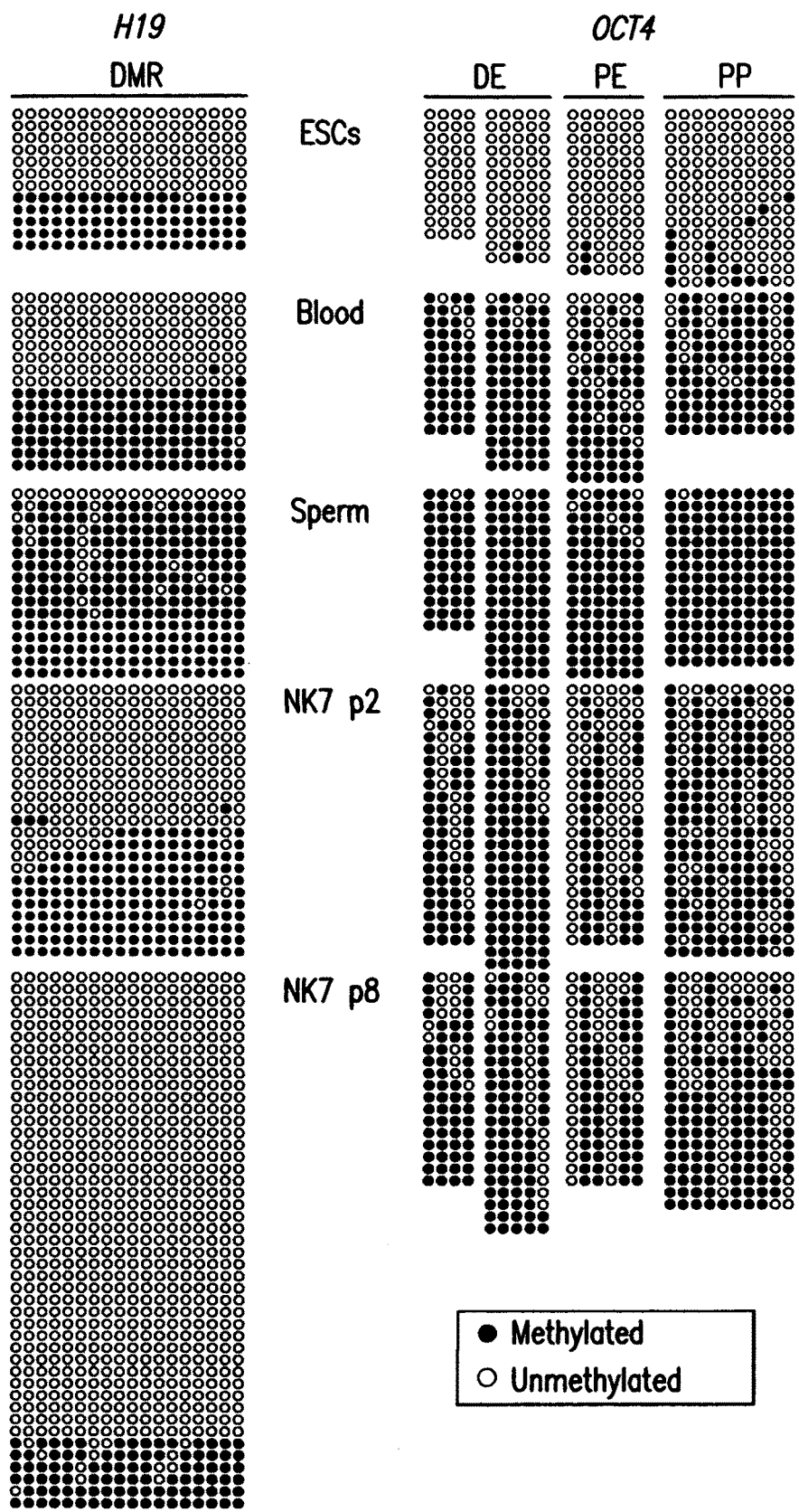
FIG. 3 illustrates bisulphite sequencing of the OCT4 promoter region and the DMR, located upstream of the H19 promoter.
Figure 3B:
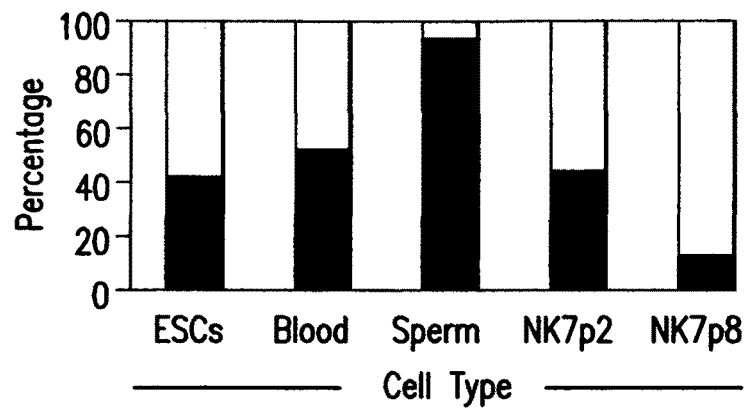
Figure 3C:
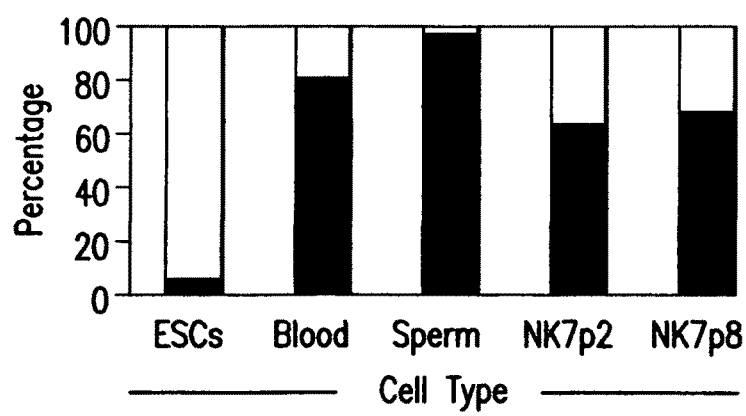

Bisulfite sequencing was performed to investigate the methylation status of 18 CpG (cytosine guanine dinucleotides) dinucleotides in the differentially-methylated region (DMR) upstream of the H19 promoter (FIG. 3A). While the maternal H19 allele is active and therefore unmethylated, the paternal H19 allele is methylated in all somatic cells. Human ESCs as well as human somatic cells carry one paternal and one maternal allele and showed a ratio of 70:30% and 50:50% unmethylated to methylated sequences, respectively, as shown (FIG. 3B-C). In contrast, in mature sperm, the paternal allele of the HI9 gene was completely methylated (100% of clones) indicative of the establishment of the unique male-specific methylation pattern at this locus during this stage of development, (FIGS. 3A,C). In contrast, when we examined the methylation status of HI 9 in NK7 hMGSCs at passage 8, we observed that this locus was hypomethylated with 87% of clones unmethylated and only 13% methylated (FIGS. 3A,C).

In addition, the DNA methylation profile of the 5'-flanking region of the human OCT4 gene was analyzed. The region investigated contains the proximal enhancer (PE), the distal enhancer (DE) and the proximal promoter (PP) as indicated in FIG. 3A. In undifferentiated cells the majority of CpG repeats in this region are unmethylated and the gene is therefore expressed. Analysis showed that 94% of CpG sites in the OCT4 promoter region of human ESCs are unmethylated, whereas only 19% of CpG repeats in blood cells and 2% of CpG repeats in sperm cells were unmethylated. Analysis of the methylation status of the OCT4 promoter region of NK7 cells at passage 2 and passage 8 showed that 36% and 32% of CpG repeats are unmethylated, respectively (FIGS. 3A,B).

This partial demethylation is in accordance with the finding that the OCT4 gene is activated in NK7 cells, as demonstrated by RT-PCR and immunofluorescence staining.

Spontaneous Differentiation

Figure 4:
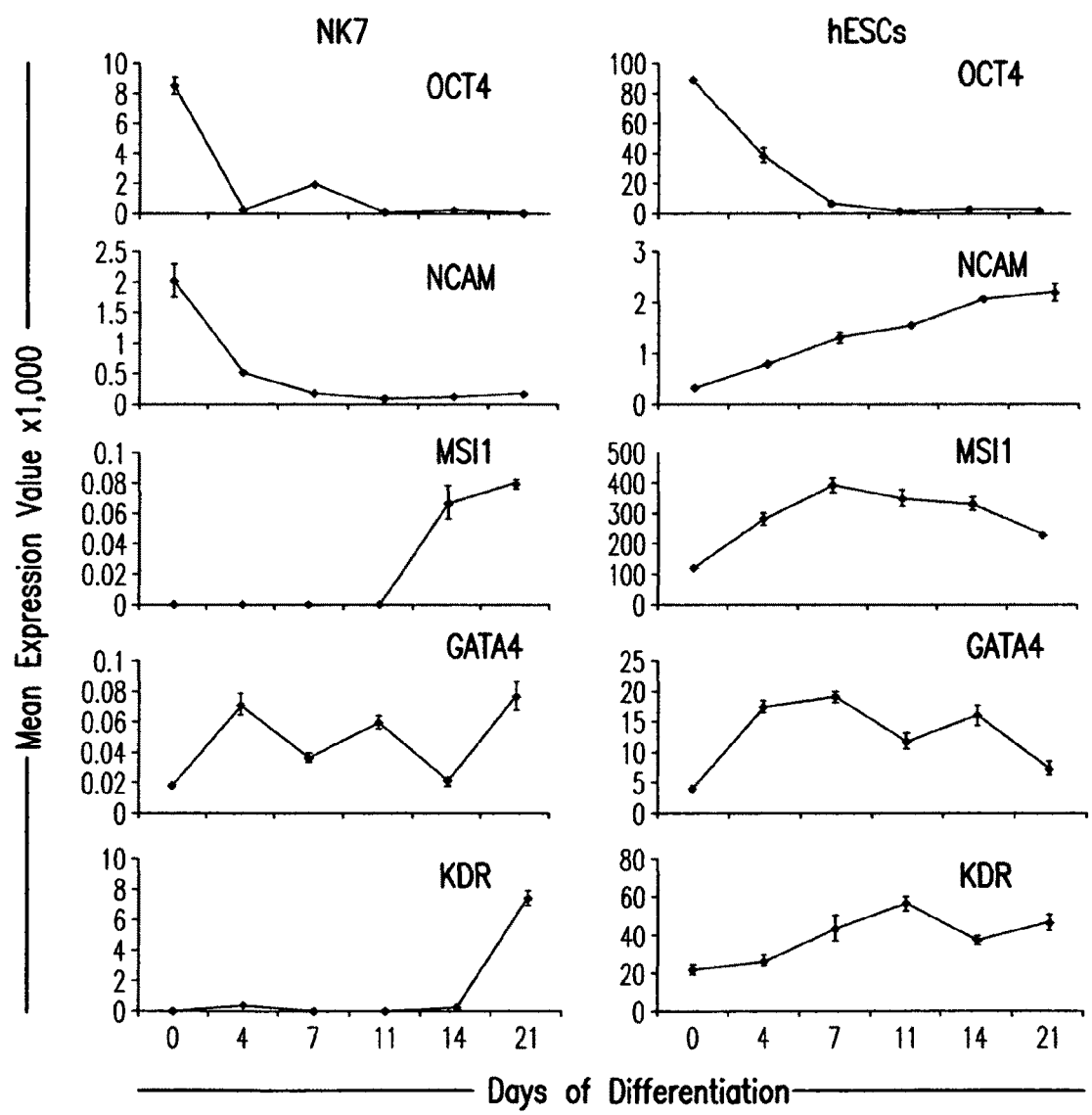
FIG. 4 illustrates in vitro differentiation of hMGSCs.

Pluripotent stem cells can self-renew or differentiate to the three primary germ layers: endoderm, mesoderm and ectoderm. To assess if hMGSCs are able to spontaneously differentiate into derivatives of the three germ layers in vitro, expression of ectoderm-, endoderm- and mesodenn-specific genes and proteins was analyzed at different time points during differentiation. H9 hESCs were used as a positive control (FIG. 4). As shown, expression of the pluripotency marker OCT-4 decreased with differentiation, with a concomitant increase in the expression of the somatic markers MSI1 (ectoderm marker), GATAQ (endoderm marker) and KDR (mesoderm marker) in both hMGSCs and hESCs.

Notably, we also found that although NCAM is commonly used as an ectoderm marker in hESC research and would thus be expected to increase with differentiation, its expression decreased with differentiation of hMGSCs. This is contrast to hESCs, which exhibited an increase in the expression levels of NCAM (FIG. 4).

Figure 5A:
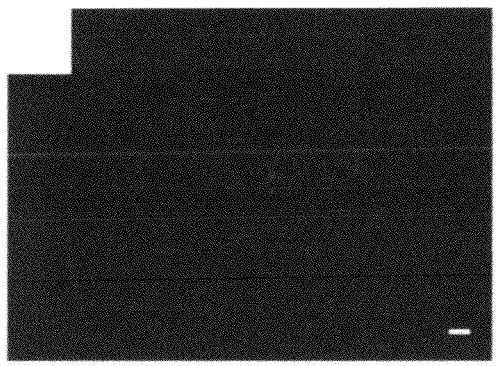
FIG. 5 illustrates immunofluoresence staining of day 7 differentiated hMGScs and teratoma analysis.
Figure 5B:
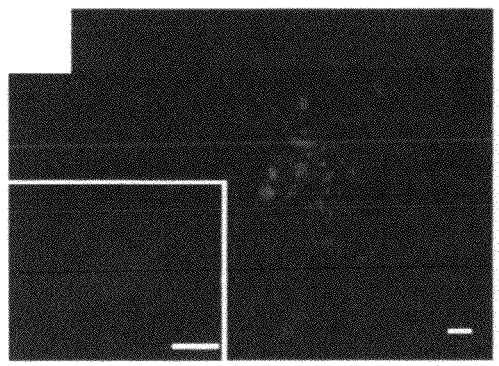
Figure 5C:
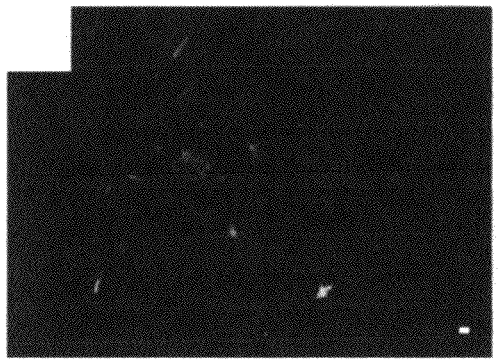
Figure 5D:
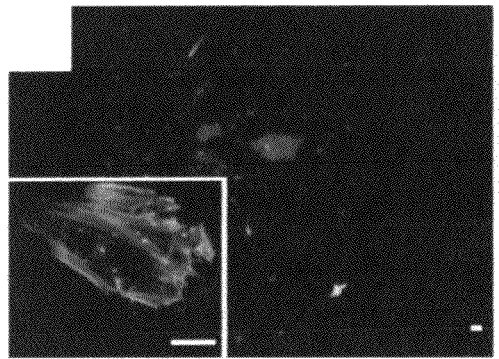
Figure 5E:
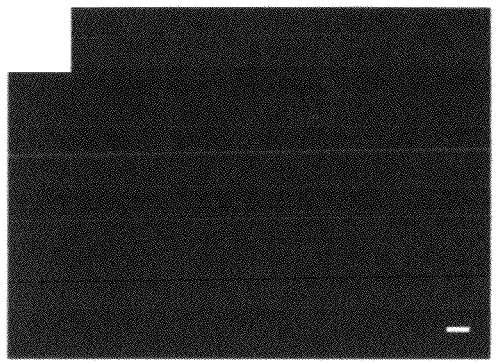
Figure 5F:
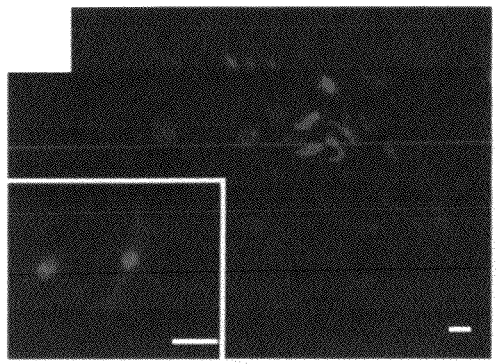

Once we examined the expression of ectoderm-, endoderm- and mesoderm-specific genes at the mRNA level, our next aim was to evaluate germ layer marker expression at the protein level by immunofluorescence. After 7 days of in vitro differentiation, differentiated hMGSCs were positive for the endoderm specific VWF (FIG. 5A-B), ACTC which specifically recognizes cardiac actin (FIG. 5C-D; mesoderm), as well as for NES, an intermediate filament that is expressed in early embryonic neuroepithelial stem cells (FIG. 5E-F; ectoderm).

Figure 5G:
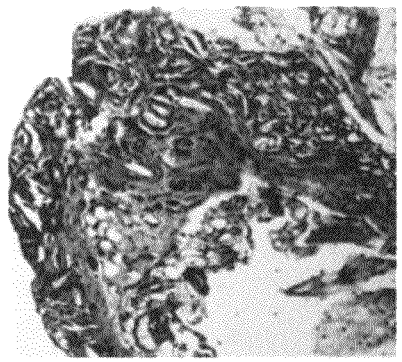
Figure 5H:
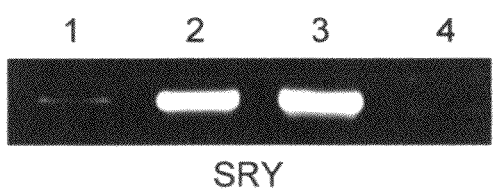

Finally, we tested the ability of hMGSCs to form teratomas under the kidney capsule of a female immunodeficient (SCID) mouse to investigate their differentiation capacity in vivo. The grafts were recovered 2 months post-transplantation and weighed 1.2 mg and 0.5 mg; histological evaluation showed that extensive teratoma formation was not detected (FIG. 5G). However, as discussed further below, human cells were present in the graft after 2 months as demonstrated by molecular analysis (FIG. 5H). PCR analysis of the human SRY human gene product indicated that the two positive control samples, NK7 genomic DNA and sperm genomic DNA contained a specific 350 bp band, as did the NK7 hMGSC graft DNA. In contrast, no specific band was amplified using female mouse genomic DNA as a template. To investigate if teratoma formation is supported by an increased cell number and/or support cells, grafts were prepared using approximately 10,000 hMGSCs accompanied by 1 million irradiated MEF cells as carrier cells. The grafts were recovered 2 months post-transplantation and histological evaluation showed no teratoma formation.

Immunofluorescence Staining Following Induced Neural Differentiation

Figure 6A:
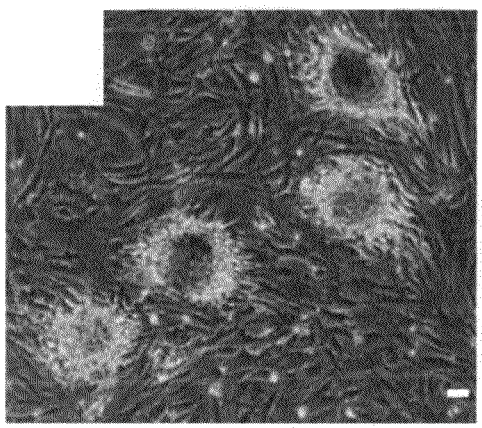
FIG. 6 illustrates immunofluorescence staining after 6 weeks of induced neural differentiation.
Figure 6B:
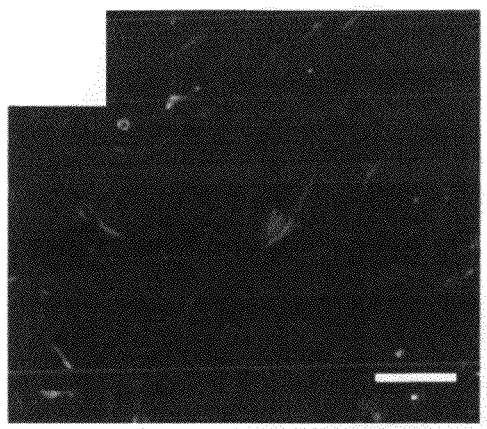
Figure 6C:
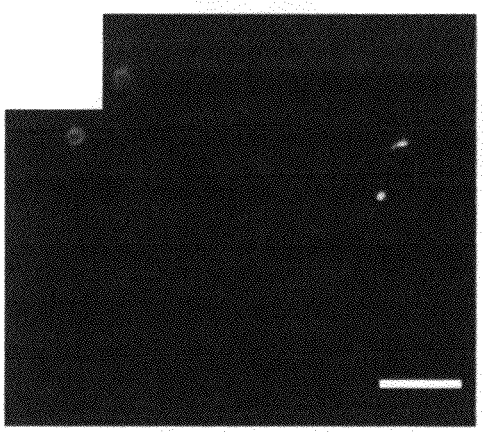
Figure 6D:
Figure 6E:
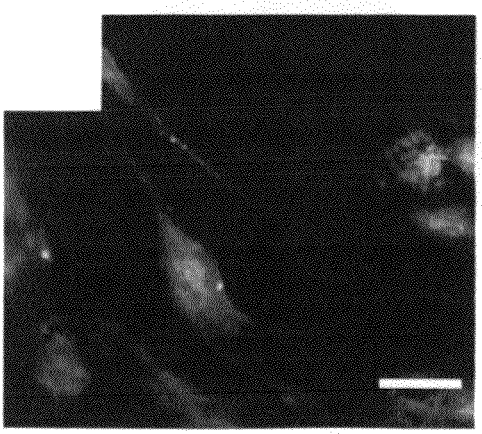
Figure 6F:
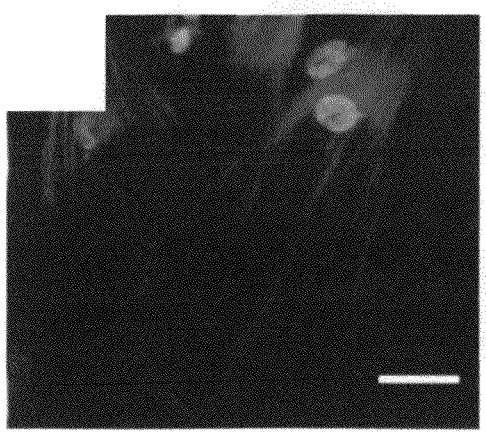

NK7 hMGSCs form colonies when they are cultured on MEFs (FIG. 6A) whereas they grow as a monolayer when they are cultured on gelatin (FIG. 6B). Prior to differentiation, the hMGSCs were plated onto gelatin and were cultured until 80% confluency was achieved. Subsequent to 6 weeks of induced differentiation to the neural cell lineage, immunofluorescence staining of neural makers was performed on the NK7 line. Cells positive for NES could be detected after the induced differentiation (FIG. 6D), but not in the untreated cell population (FIG. 6C). In addition, cells stained positive for MAP2 (FIG. 6E) and TUB 111 (FIG. 6F) demonstrating that NK7 hMGSCs have the potential to differentiate towards the ectodermal lineage.

Discussion

Standard methods of generating hESC lines are limited in ability to generate patient- or disease-specific lines of potential use for both basic science and clinical applications.

However, over the years, elegant studies have shown that in model organisms and/or humans, somatic cells can be reprogrammed to an undifferentiated state via methods such as somatic cell nuclear transfer (SCNT), somatic cell fusion with embryonic stem cells and induced pluripotent stem cell technology. In addition, recent reports have documented the derivation of pluripotent stem cells from both neonatal and adult mouse testis. In these mouse studies, pluripotent stem cells were derived without genetic modification via enrichment for spermatogonial stem cells subsequent to reprogramming of multipotent germline stem cell (mGSC) colonies in culture. The resulting cells were shown to differentiate extensively to all germ layers and the germ line, bearing resemblance to mouse embryonic stem cells (mESCs).

In this study, we isolated pluripotent cells from human testis biopsies that were manually transferred onto MEFs and cultured under hESC culture conditions. On MEFs, the cells maintained the ability to form colonies for at least 17 passages. The colonies were characterized by a classic stem cell-like morphology on plates and the formation of EB-like structures, in suspension. Based on the results described above, we propose that these cells are hMGSCs.

Diagnostic Gene Expression

The hMGSCs derived here expressed the pluripotency markers OCT-4 and SOX-2, but not NANOG. The apparent lack of NANOG expression is in agreement with the cell origin and NANOG expression pattern in adult testis in both humans and mice. It is known that NANOG expression is regulated by the binding of OCT-4 and SOX2 to the NANOG promoter region and it has therefore been suggested that all three proteins function as regulators to maintain pluripotency. Recent studies demonstrated however, that Nanog expression is not essential for self-renewal or the differentiation potential of embryonic stem cells, but that instead, it plays a role in establishing the inner cell mass and germ cells in vivo and that it enhances self-renewal of embryonic stem cells. In addition to OCT-4 and SOX2, the expression of other genes such as STELLAR, GDF3, PUMI, PUM2, DAZL, SCP3 and MLH1 was consistent with a germ-cell origin of the hMGSCs. In contrast, expression of a late marker of male germ cell development (TEKTI) was not detected. This expression pattern demonstrates that hMGSCs express pluripotency markers, early-stage germ cell markers and a subset of later-stage germ cell markers. Furthermore, the distinct expression patterns of NK7 cells grown under ESC culture conditions and NK7 cells grown on human testicular stromal cells indicate that NK7 cells can be reprogrammed to hMGSCs, as demonstrated by SOX2 expression and the loss of late germ cell marker expression.

Spontaneous Differentiation In Vitro

The results from spontaneous differentiation in vitro clearly demonstrated that hMGSCs have the potential to differentiate into derivatives of the three primary germ layers in vitro. When transferred to differentiation media, the expression of OCT-4 decreased dramatically in hMGSCs as well as in hESCs, in parallel. We also noted that the expression of NCAM which has been used as an ectodermal marker for hESC differentiation, decreased during in vitro differentiation of hMGSCs. Although this was initially unexpected, closer scrutiny indicated that NCAM is expressed in male germ line cells and may function in spermatogonial stem cells, as a receptor for GDNF, as described. Thus, the decrease in NCAM expression further supports the results of somatic differentiation, as indicated by the increase in expression of the somatic differentiation markers MSII, GATA4 and KDR at both the RNA and protein levels. These markers have previously been shown to be expressed solely in differentiated hESCs.

The differentiation potential of NK7 hMGSCs was further demonstrated by induced neural differentiation. Following 6 weeks of culture in neural cell specific media, the expression of NES, MAP2 and TUB 111 could be detected.

STRNNTR, Karyotype and Telomerase Activity

We observed that the karyotype of the putative hMGSCs, as well as the somatic cells of the patient who donated the biopsy, was normal. Furthermore genetic analysis indicated that the hMGSCs were undoubtedly derived from the testis biopsy of the man who donated the sample for research and not a laboratory/cell contaminant. There was no evidence of common karyotypic abnormalities associated with germ cell tumors, such as amplification of chromosome 12p. In addition to normal karyotype, hMGSCs possess telomerase activity in vitro. In immortal cells, such as hESCs, germ cells or cancer cells, the shortening of telomere length is prevented by telomerase. In this study, we observed a decrease in telomerase activity after two consecutive passages that may indicate that the current culture conditions require further optimization to enhance proliferative capacity, or stability, of the spermatogonial stem cells in vitro. Other cell types, including somatic cells and sperm demonstrated little or no telomerase activity, as expected. These findings parallel those in mice.

Methylation Analysis

To further probe origins and status of the hMGSCs, we examined methylation of the imprinted locus, H19, a locus normally expressed differentially from the male and female gem line. Numerous studies over the years have demonstrated that HI9 is methylated in the male germ line; nonetheless, the timing of imprint erasure and the re-establishment of the male-specific methylation pattern in human germ cell development has not been completely elucidated. It seems most likely that de novo methylation is established before the germ cells enter meiosis. Results of methylation analysis described above showed a ratio of 70% unmethylated to 30% methylated in hESCs, in line with previous studies of hESC imprints, and 50% to 50% in human blood cells, as expected, 391. Moreover, sperm cells carry only the paternal allele of the H19 gene and were 100% methylated, which is also in agreement with published findings. The hMGSCs, however, were hypomethylated with 87% of the clones being unmethylated and only 13% methylated suggesting that either a subpopulation of germ cells (such as PGCs), devoid of methylation, gave rise to the hMGSCs or alternatively, that reprogramming of the hMGSCs led to imprint erasure.

Recent studies have shown that reprogramming of somatic cells is associated with demethylation of OCT4 regulatory regions with the most apparent changes occurring in PE-, the DE- and the PP-region. Mosaic CpG demethylation has been shown to be physiologically important as it leads to the activation of the gene. Analysis of the methylation status of the OCT4 promoter region of NK7 cells at passage 2 and passage 8 demonstrated that 36% and 32% of CpG repeats are unmethylated. This partial demethylation is in agreement with the activation of the OCT4 gene and supports the theory that human spermatogonial stem cells are multipotent when cultured under human ESC culture conditions.

Teratoma Assay

The results of in vivo differentiation analysis merit further comment. We observed that hMGSCs did not induce formation of a large teratoma (which may or may not be beneficial for putative clinical applications). Nonetheless, PCR analysis using primers specific for the human SRY gene indicated the presence of human cells in the graft even after 2 months. The most likely explanation for this finding is that some of the human cells persist but that a larger number of cells is required for further teratoma analysis (4000, as used here, is at the lower limit of detection without MEFs serving as a carrier). Repetition of the teratoma assay using 10,000 hMGSCs accompanied by 1 million irradiated MEF cells did not lead to teratoma formation after transplantation even though 500-1000 murine embryonic stem cells accompanied by 99 000 MEFs have been shown to be sufficient to induce tumor growth. These results indicate that while hMGSCs appear to have the potential to differentiate into derivatives of the three germ layers upon spontaneous or induced in vitro differentiation, they may not have been reprogrammed sufficiently to generate teratomas.

The ability to isolate and culture hSSCs in vitro facilitates development of novel therapeutic strategies for the treatment of infertility. For example, one side effect of cancer treatments is the potential destruction of SSCs, along with the cancer cells, with the possibility of leaving the patient infertile. To maintain fertility, testicular biopsies may be obtained prior to the treatment, SSCs may be propagated in vitro and finally transplanted back into the patient's testis when the treatment is completed, if germ cell development can be controlled.

In Vitro Maturation of Adult Human Germ Cells to Haploid Cells in a Biological Environment The maturation of early human germ cells to mature sperm in vitro has been attempted but has not been successful to date. Duplicating the complex testis environment in which germ cell maturation occurs has proven a difficult task in the laboratory and is likely the reason for the lack of success. The present inventors herein describe the use of primary adult human Sertoli cell cultures to provide an essential and sufficient environment to produced human sperm from spermatogonial stem cells (SSCs). It has been discovered that confluent non-proliferative Sertoli cells are an advantage matrix for the initial isolation and culturing of adult human SSCs.

Spermatogenesis

Spermatogenesis consists of four sequential interdependent processes involving several types of germ cells and Sertoli cells. First, spermatogonial proliferation and differentiation of $A_{dark}$ and $A_{pale}$-spermatogonia occurs. Then, their is division of committed $A_{pale}$-spermatogonia to form B spermatogonia, followed by their division to form preleptotene spermatocytes. Second, a round of DNA synthesis occurs in preleptotene spermatocytes followed by two meiotic divisions resulting in spermatid formation. Third, spermiogenesis occurs with dramatic, complex and ill-understood changes in cell morphology and transformation of spherical to elongated spermatids and finally to mature sperm. Lastly, spermiation involves the physical release of spermatids from Sertoli cell into the tubule lumen. Sertoli cells support the entire process of spermatogenesis as germ cell maturation occurs within and between these nurse cells. Sertoli cells also form the physical blood testes barrier that is immunologically protective of germ cells. This barrier is also is a dynamic one that must regularly break down and reform between adjacent Sertoli cells near the basal lamina as developing, post-meiotic germ cells move into the adluminal compartment. In humans, the entire process from proliferation of committed A-pale spermatogonia to spermiation of resulting spermatozoa requires 74 days.

Other factors also play a role in spermatogenesis. 6-integrin and 1-integrins have been postulated to anchor spermatogonial stem cells onto the tubular basement membrane. Extracellular matrix components produced by peritubular myoid cells are fibronectin, collagen I, chondroitin proteoglycan, while Sertoli cells produce laminin, collagen I and IV, chondroitin proteoglycan, and heparin. Known growth factors also appear to be important for spermatogenesis. Even though various growth factors have been tested to induce proliferation in rat and mouse spermatogonial stem cells in serum-free media, studies in mouse, rat, bovine, and monkey have conclusively shown that while GDNF is required in growth medium for SSC maintenance, GDNF and FGF2 containing serum-free formulation may be most effective in supporting spermatogonial proliferation when EGF and LIF are not present. Thus the maturation of SSC's to haploid cells is a highly complex spatial and temporal biological program that is best attempted in vitro in a suitably adjusted Sertoli cell environment.

Upon co-culturing the human SSCs (hSSCs) with/on Sertoli cells, the present invention explicitly contemplates in vitro maturation of the hSSCs to haploid germ cells, i.e., the differentiation of hSSCs through the spermatogenic pathway to round spermatids, elongating spermatids or mature sperm. This pathway or sequence of differentiation includes hSSCs to primary spermatocytes to secondary spermatocytes to spermatids (haploid cells) to mature sperm.

Hereinbelow is described various protocols for isolation of adult human SSCs, and in vitro maturation thereof in a biologically-supportive matrix.

Protocol:

Isolation of Adult Human SSCs

A small piece of testicular tissue (biopsy size) is collected aseptically in serum-free Dulbecco's modified Eagle's Medium (DMEM, high glucose). As needed, interstitial cells and blood vessels are removed by shaking and washing. The first enzymatic digestion is with collagenase IV (Sigma, St. Louis, Mo.) and DNase I (Sigma; 1 mg/mL and 2 µg/µL, respectively). The isolated seminiferous tubules are further digested with collagenase IV, hyaluronidase (Sigma), and trypsin (Sigma) at the concentration of 1, 1.5, and 1 mg/mL, respectively, to obtain individual cells, and then centrifuged to pellet the spermatogonia and somatic cells as shown in FIG. 1. These cells are then either be co-cultured with Sertoli cells as shown in FIG. 1A or further purified before co-culture with Sertoli cells as shown in FIG. 1B. The additional purification could incorporate either positive selection or negative selection by immunoaffinity and magnetic activated cell sorting (MACS). The MACS could be based on anti-biotin beads and biotinylated antibody to spermatogonial cell surface proteins. We first evaluate positive selection with CD49f ($\alpha_6$ integrin; BioLegend) as previously described. Secondly, we use positive selection with biotinylated antibody to other cell surface makers such as CD9 or GFr-alpha-1. In addition, negative selection with MACS may be used, for example, with biotinylated antibodies to cell surface markers on Sertoli cells such as FSHr that should not be expressed by SSCs.

Co-Culture with Human Sertoli Monolayers.

In one embodiment human Sertoli cells (passage ≤5) are plated in six-well plates (~5,000 cells/well) and grown to confluence in Dulbecco's-modified Eagle's medium (DMEM)-high glucose:Ham's F-12 50:50 with 0.15-5% fetal bovine serum or KnockOut Serum Replacer (Invitrogen). The cell suspensions containing the spermatogonial cells to be used for spermatogenesis will be seeded in Knockout ES medium onto the normal cell culture plates (containing confluent monolayers of Sertoli cells) at $0.1$-$0.5 \times 10^6$ cells per $cm^2$. The plates will be centrifuged to spin down adherent cells to change media. Various markers may be used for purification of SSCs. Some exemplary positive and negative markers are listed below in Table 1.

TABLE 1

CONDITIONS AND MARKERS THAT COULD BE USED FOR SSC PURIFICATION

| MACS selection (mAb binding) | Matrix Selection | Analysis | Specific Markers | |
|---|---|---|---|---|
| Positive | Negative | Alk phosphatase activity | Negative | Positive |
| CD9, CD49f, GFRalpha-1 | collagen, fibronectin | Cell-specific RT-PCR | (Sermatogenic) Acrosin, Protamine, LDH-C4 | CD9, GPR125, DAZL, Oct-3/4, VASA, Notch-1. |

TABLE 1-continued

CONDITIONS AND MARKERS THAT COULD BE USED FOR SSC PURIFICATION

| MACS selection (mAb binding) | Matrix Selection | Analysis | Specific Markers |
|---|---|---|---|
| Negative FSHr. | Positive laminin | Immunostaining FACS (after expansion) | (Somatic) CD105, vimentin, Sox9, GATA4 (Hematopoietic) CD34, Cd45 |

Figure 8:
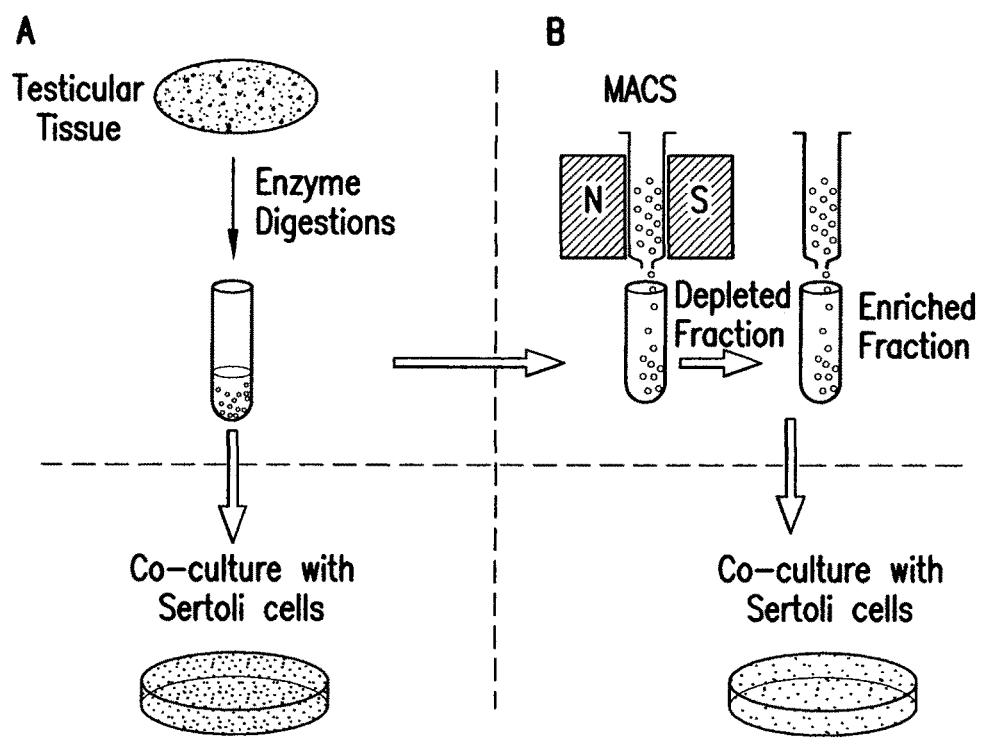
FIG. 8 illustrates isolation of spermatogonial stem cells (SSCs).
Figure 9:
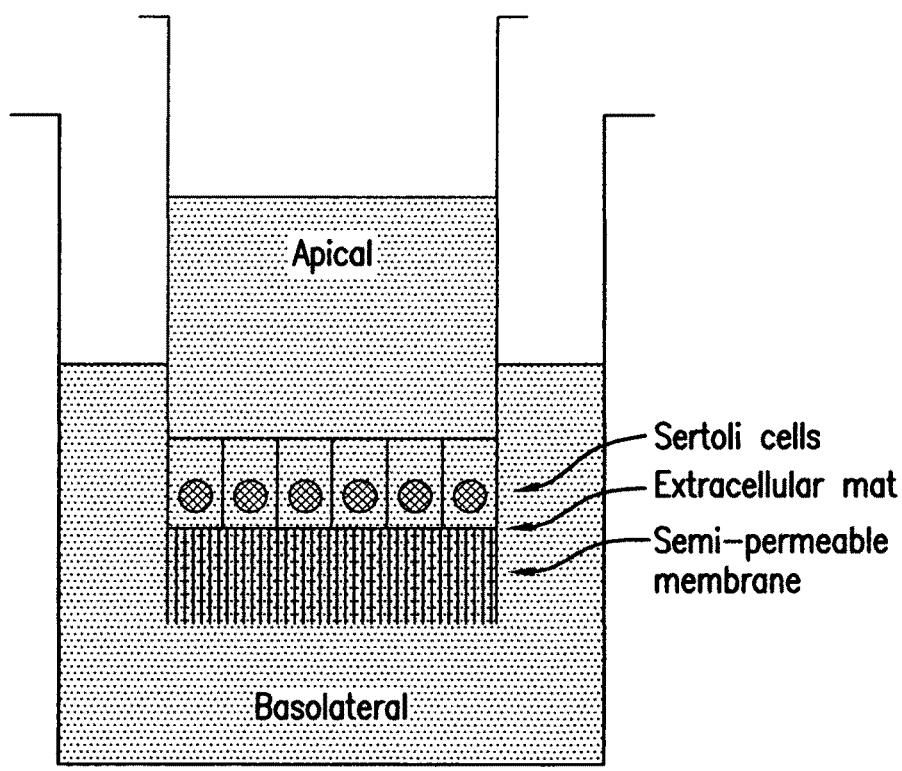
FIG. 9 illustrates a transwell insert culture.

In other embodiments the testicular cell suspensions formed as illustrated in FIG. 8 are co-cultured with Sertoli cells growing on extracellular matrix such as Matrigel, (BD Biosciences, Two Oak Park, Bedford, Mass.) or purified extracellular matrix protein in polarized monolayers on transwell inserts as shown in FIG. 8, or in or on hollow-fiber capillaries as illustrated in FIG. 9.

Co-Culture with Polarized Human Sertoli Cells Growing on Semipermeable Membranes in Transwell Inserts.

In another embodiment, transwell inserts will be incubated with a dilute solution of extracellular matrix protein overnight at room temperature. After removal of the solution, human Sertoli cells (passage ≤5) will be seeded (approximately $0.5 \times 10^6$ cells/cm$^2$) into transwell chambers and cultured in DMEM:Ham's F12 with 5% fetal bovine serum or KnockOut Serum Replacer at 37° C. for seven days. A schematic of the transwell insert is illustrated in FIG. 9. These can be made for use with 6, 12, 24, or 96-well plates and are available from various vendors with a variety of pore sizes. In a preferred embodiment, the pore size is 0.4 µm. The transwell culture system is well known to those skilled in the art of mammalian cell culture.

Polarized Sertoli cells could be prepared in 12-, 24-, or 96-well plates in transwell inserts that can be obtained available from vendors including Corning (Lowell, Mass.), Millipore (Danvers, Mass.), and BD Biosciences (San Jose, Calif.) in pore sizes ranging from 0.4, 1.0, 3.0 to 8.0 µm. The transwell inserts should be coated with extracellular matrix protein, such as a dilute solution of Matrigel™ Basement Membrane Matrix (Bd Biosciences), for example diluted 1:7 vol:vol in cell culture medium or a purified extracellular matrix protein such as laminin or fibronectin [2] dissolved (for example, 10 µg/ml) in serum-free medium such as DMEM. Approximately 30-300 µL of the solution can be added to each insert and these are then incubated for an hour up to overnight. After removing the excess solution from the inserts, the cells can be seeded (~$1.2$-$1.5 \times 10^6$ cells per cm$^2$) in cell culture medium such as DMEM:Ham's F12 50:50 with 5% fetal bovine serum. The formation of tight junctions would require 3-7 days and can be assessed by the lack of hydrodynamic equilibrium, by restricted diffusion of molecules such as $^{125}$IBSA and Lucifer yellow from the apical to basalateral chamber, by the detection of the polarized secretion of Sertoli cell proteins, and by increase in the transepithelial electrical resistance (TER) which is measured by a epithelial volt ohmmeter (Millipore). The TER should be in the range of 100-145 ohms per cm$^2$ after subtracting the TER for no-cell control wells in the absence of supplemental hormones as generally described for rat Sertoli cells. Supplements such asFSH (100-200 ng/ml) and testosterone (~20-200 nM) also can be added to the media and should cause some increase in the TER.

The cell suspensions containing the spermatogonial cells to be used for spermatogenesis will be seeded in Knockout ES medium into the apical chamber of the transwell inserts (containing confluent monolayers of Sertoli cells) at $0.1$-$0.5 \times 10^6$ cells per cm$^2$. The cells can be fed so as not to disturb them by media placed in the basolateral compartment.

Co-Culture with Polarized Human Sertoli Cells Growing on Hollow Fibers.

Figure 10A:
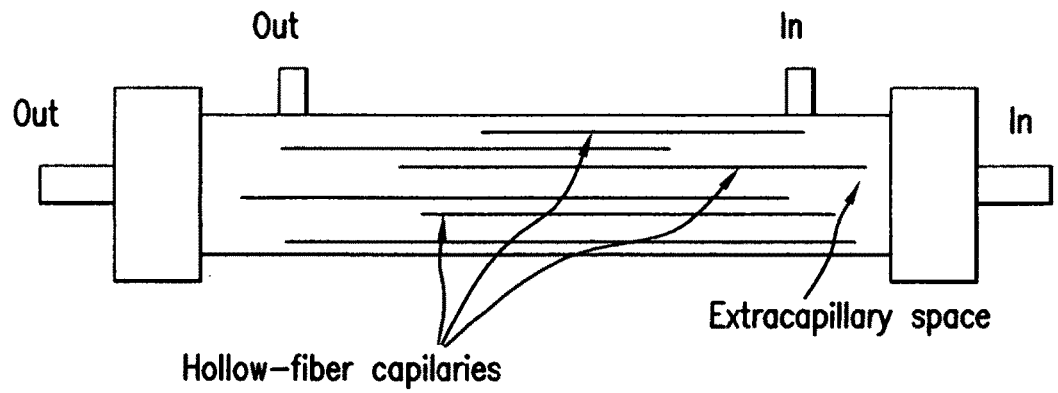
FIG. 10 illustrates a hollow-fiber capillary culture.
Figure 10B:
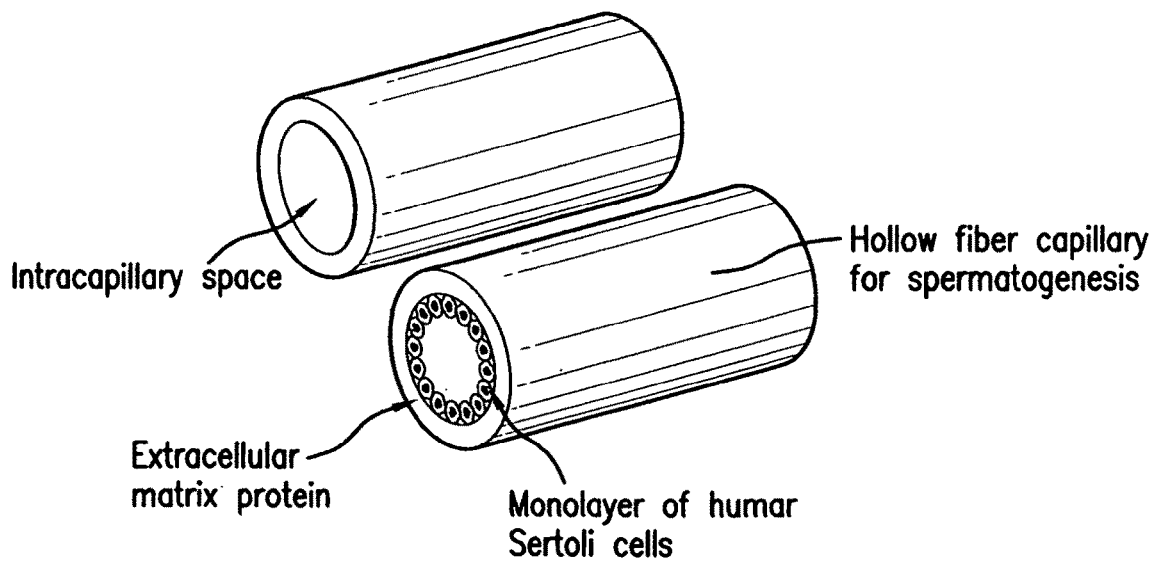

In an alternative embodiment, the Sertoli cell co-culture could be performed in (or on) hollow-fiber capillaries (0.2-1.0 mm internal diameter) that are semipermeable, and have an interior (or exterior) surface coated with extracellular matrix protein on which a monolayer of Sertoli cells is cultured (approximately $0.5 \times 10^6$ cells/cm$^2$) as shown in FIG. 10. Such capillaries could be placed in a cartridge that is connected to a pump for infusion of cell culture medium and supplements. Similar systems have been adapted for culture of many different types of cells. The cell suspensions containing the spermatogonial cells to be used for spermatogenesis will be seeded onto the monolayers of confluent Sertoli cells in Knockout ES medium at $0.1$-$0.5 \times 10^6$ cells per cm$^2$.

Generally, extracellular matrix protein may be attached to the surface of the intracapillary space by any of the methodologies as described in U.S. Pat. No. 5,872,094 and U.S. Pat. No. 6,471,689, both of which are incorporated herein in the entirety by reference.

Further, Sertoli cells may be deposited and cultured on the deposited extracellular matrix protein by any methodology as described in U.S. Pat. No. 5,508,188 and/or U.S. published patent application 2009/0104593, and 2009/0028833, all of which are incorporated herein by reference in the entirety.

Transwell models do not provide a continually renewed supply of nutrients, oxygen and waste product removal, and do not mimic blood flow and shear stress patterns that have been shown to induce differentiation of endothelial cells and the differentiation and maintenance of the barrier phenotype. In the absence of shear stress, endothelial monolayers degenerate with prolonged culture due to the cellular apoptosis. Hollow-fiber cell culture systems can induce the polarization of cells and provide flow along with shear stress. Advantages that, have been demonstrated in the growth of polarized cells forming tight junctions such as models of the blood-brain barrier (BBB) in hollow-fiber flow systems compared to transwell systems include significantly increased TER, decreased permeability to test molecules such as $C^{14}$inulin, and much longer lifetimes for the cultures. This would be advantageous for the creation of an in vitro device for spermatogenesis with sustained lifespan or use cycle.

Similar to the blood-testis barrier that is formed by Sertoli cells in the testis is the BBB. A hollow-fiber flow system developed for modeling the BBB using a human brain endovascular cell line can be modified to model the blood testis barrier (BTB) with Sertoli cells and used as an environment for differentiation of germ cells. In this setting, first the Sertoli cells are cultured and the formation of tight junctions confirmed prior to introduction of the spermatogonial stem cells.

Briefly, modules can be obtained from Spectrum (Cat.#400-025, Rancho Dominguez, Calif.) that consist of a bundle of 50 hollow polypropylene fibers that are in a clear plastic accessible chamber (cartridge) surrounding the fibers, and the Sertoli cells are seeded inside the hollow fibers. The semipermeable (porous) walls of the fibers enable the exchange of gas ($O_2$ and $CO_2$) and nutrient exchange between the "luminal" and the "abluminal" compartments, but does not allow the passage of cells. Both compartments areas are accessible by ports that connect to a medium reservoir and a pulsatile pump as known. Gas exchange occurs via silicone tubing that connects the chamber and the medium reservoir. A pair of electrodes in the luminal and in the abluminal compartments could connect to a computerized system for real-time quantification of TER. The pump circulates the medium and nutrients are exchanged between compartments by diffusion through capillary-like 0.5 mm pores. The pump can be adjusted for flows of medium from 1 to 50 ml/min (shear stress levels of ~1 to 200 $dyn/cm^2$). The apparatus is kept within an incubator to maintain precise temperature control and 5% $CO_2$. For monitoring the culture, medium samples from the luminal and abluminal compartments will be taken every 2 days and processed for glucose consumption and lactate production.

The lumens of the hollow fibers can be pre-coated with extracellular matrix proteins in a manner similar to the transwell systems. For example, the lumens could be coated with Matrigel (diluted 1:7 vol:vol) fibronectin (~3 $mg/cm^2$), or collagen 5 $mg/cm^2$ to enhance Sertoli cell attached as described for the BBB model system.

The Sertoli cells can be seeded intralumenally at $4 \times 10^6$ cells/cartridge. After waiting for cell adhesion from 2-4 days after cell inoculation the flow rate will be increased to a steady-state level such as ~4 mL/min (i.e., 4 $dyn/cm^2$). This will be adjusted again upon inoculation with the spermatogonial cells lowering the flow rate to allow their adherence to the Sertoli cells within the lumen of the hollow-fiber cartridge. The rate would be increased after the adherence of the spermatogonia and again to facilitate the harvesting of the mobile haploid spermatocytes from within the chambers.

TABLE 2

COMPARISON OF TRANSWELL AND HOLLOW FIBER CULTURE

| Transwell Culture | Hollow Fiber Culture |
|---|---|
| Plate on monolayer of human Sertoli cells growing on extracellular matrix in transwells inserts in 6, 12, 24, or 96-well plates | Culture with monolayers of Sertoli cells growing on top of or inside hollow-fibers coated with extracellular protein |
| Culture in medium with gonadotropins | Culture in medium with gonadotropins |
| Enzymatically digest and use magnetic cell separate to deplete somatic cells | Use force of flow to selectively elute spermatozoa |

These hollow-fiber bioreactor systems can be adapted to culture of a variety of cell types. Hollow-fibers have been developed by the National Cancer Institute of the National Institutes of Health for growing cancer cells and evaluation in vivo of the response to anticancer drugs. A custom-designed hollow-fiber capillary culture system could be manufactured using readily available materials for mammalian cell culture on a contractual basis by many different vendors. Some types of hollow-fiber systems for cell culture are commercially available from companies, for example, FiberCell Systems, Inc. (Frederick, Md.). The hollow fiber systems made by FiberCell Systems are composed of fibers that are approximately 200 microns in diameter similar in diameter to that of seminiferous tubules. The fibers are sealed into a cartridge that is designed so that cell culture medium pumped through the end of the cartridge flows through the inside of the fiber. The cells are attached to a porous support and the cultures can be maintained for many months of continuous production.

Propagation, Purification and Analysis of Haploid Germ Cells.

Co-culture will be carried out for 74 days or more to obtain haploid germ cells. The cells will be grown in DMEM high glucose medium containing 15% knockout serum replacement for ES cells (Gibco/Invitrogen), 2 mM 1-glutamine (Gibco/Invitrogen), 0.1 μM β-mercaptoethanol (Sigma), 100× non-essential amino acids (Gibco/Invitrogen), 1× penicillin-streptomycin (Gibco/Invitrogen), 10 ng/mL bFGF (BD Biosciences, Bedford, Mass.), and 0.12 ng/mL TGF-β (BD Biosciences) as described. The cell culture medium also will be supplemented with gonadotropins 5 I.U (International Units) per liter, recombinant follicle stimulating hormone (rFSH), 5 I.U. human chorionic gonadotropin (hCG), and testosterone (20 nM). Haploid cells are harvested from the Sertoli and other somatic cells by negative MACS selection.

Figure 11:
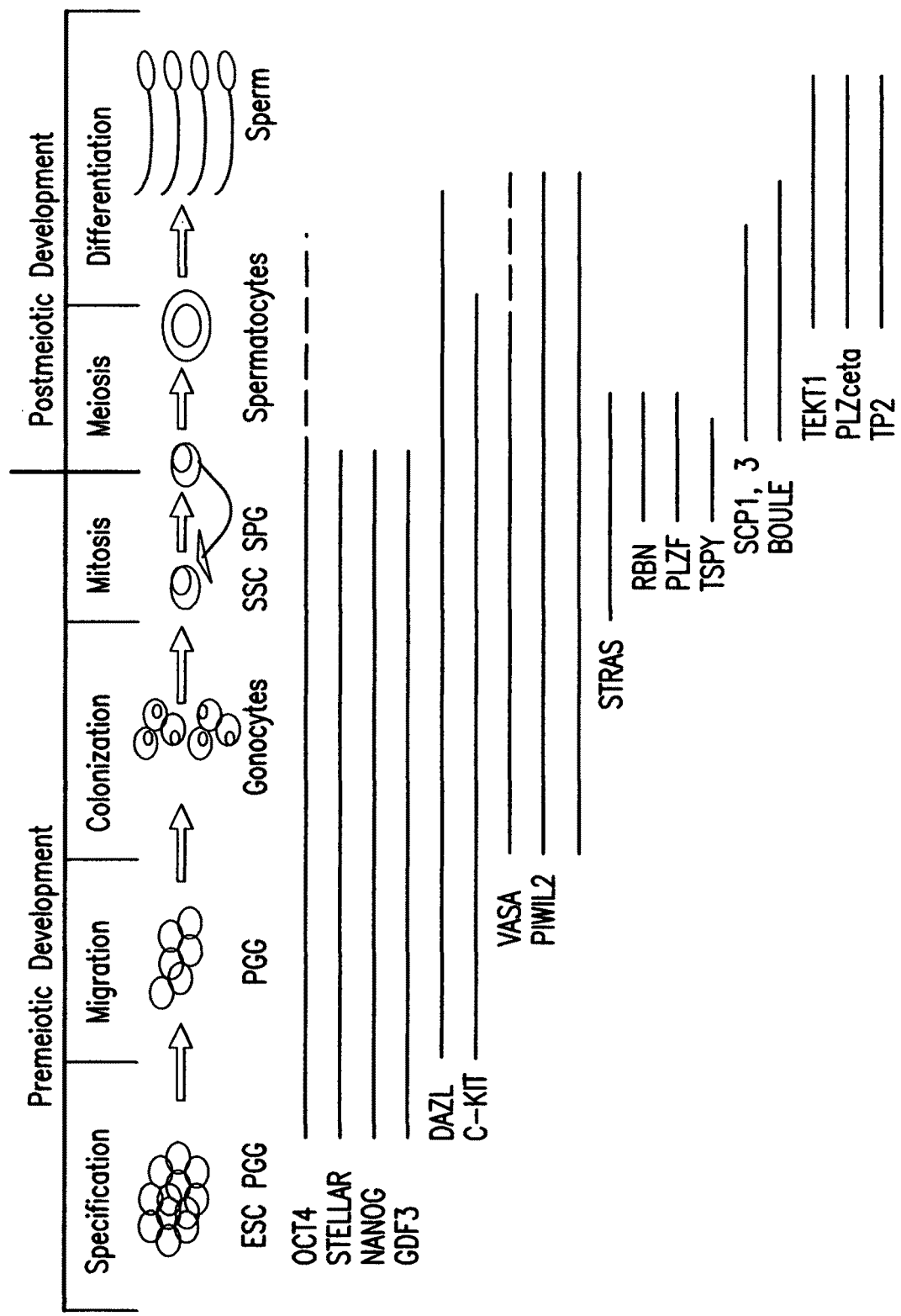
FIG. 11 illustrates various markers expressed during spermatogenesis.

The sample supernatant and monolayers are periodically monitored for (a) cell morphology, (b) ploidy and (c) in situ hybridization for germ cell markers. Haploid cells are identified by ploidy analysis and expression of stage specific markers (FIG. 11). Sperm are identified morphologically after differential staining to look for acrosome and tail. Germ cell differentiation are assayed by flow cytometry using propidium iodide staining to assess ploidy. Cells are separated into diploid (2C), double diploid/tetraploid (4C) and haploid (IC) cell fractions. Tetraploid (4C) cells are primarily spermatocytes.

Analysis of haploid cells may include expression of spermatogenic markers such as acrosin, protamine, and or others such as TEK1, PLZceta and TP2 as shown in FIG. 11. In addition, the lack of expression of hematopoietic markers such as CD34 and CD45, and markers for Sertoli and other somatic cells such as Sox9, and GATA4 may be analyzed.

Spermatogenesis

The figures of the present specification will now be described in detail.

FIG. 1. Morphological analysis and analysis for the expression of both pluripotency and germ cell specific markers. (A): Light microscopy of spermatogonial stem cells colonies growing on top of a monolayer of testicular cells approximately 2 weeks after plating of the testicular cell suspension. (B): After 6 passages in culture. (C): Spermatogonial stem cells in suspension (D): a. Expression analysis of embryonic stem cell and germ cell specific markers in NK7 hMGSCs cultured on MEFs after 2 passages and 7 passages 5. c. Expression analysis of NK7 cells cultured on human testicular stromal cells after 10 passages and of a commercially available testis sample d. Shown are RTPCR products separated by gel electrophoresis. (E-H): Immunofluorescence staining of hMGSCs passage 8, for pluripotency markers: (E): SSEA4. (F): TRAI-81. (G): Staining of hMGSCs passage 8 for embryonic stem cell and germ cell specific marker alkaline phosphatase. Shown are two colonies with different morphologies. (H): OCT-4. (I): SOX2. (J): Staining of hMGSCs passage 8 for embryonic stem cell and germ cell specific marker DAZL. FIGS. (E), (F), (I) and (J) show the co localization of DAPl with the corresponding pluripotency-germ cell marker on the left side and the respective marker on the right side of the image. Scale bars represent 50 pm.

FIG. 2. hMGSCs have a normal karyotype and express telomerase. (A): The DNA spectral karyotyping experiment of undifferentiated hMGSCs passage 8 demonstrates a normal (46,XY) karyotype. The spectral image, the DAPl staining and the resulting chromosome table are shown. (B):

Telomerase activity was investigated in hMGSCs passage 6 (NK7A) and passage 8 (NK7B) using the TRAPEZE ELISA assay. A cell extract from HSF8 hESCs served as a positive control for this experiment. The telomerase activity was calculated as average change in absorbance of the sample at 450 nm minus the absorbance at 690 nm. The black bars represent the samples without heat treatment while the white bars represent the samples with heat treatment.

FIG. 3. Bisulphite sequencing of the OCT4 promoter region and the DMR, located upstream of the H19 promoter. (A): Methylation profile of the human OCT4 and HI9 gene. Each row of circles represents a single cloned allele and each circle represents a single CpG site (white circle, non-methylated cytosine; black circle, methylated cytosine). Bisulphite-modified DNA from H9 hESCs, hMGSCs (NK7) passage 2 and passage 8, blood cells and sperm cells were analyzed. (B): Percentages of clones methylated and unmethylated present in the promoter region of the OCT4 gene, as portrayed in (A) above. White bars indicate the percentage of unmethylated clones while black bars indicate the percentage of methylated clones for each cell type as shown along the X axis. (C): Percentages of clones methylated and unmethylated present in the DMR of the H19 gene, as portrayed in (A) above. White bars indicate the percentage of unmethylated clones while black bars indicate the percentage of methylated clones for each cell type as shown along the X axis.

FIG. 4. In vitro differentiation of hMGSCs. Human MGSCs and H9 hESCs were spontaneously differentiated in vitro over a period of 21 days. RNA was isolated at 6 time points and TaqMan RT-PCR was performed to quantify the expression of the pluripotency marker OCT-4 and the somatic genes NCAM, MLHI (ectoderm marker), GATA4 (endoderm marker) and KDR (mesoderm marker). Expression values were calculated as outlined in reference and were normalized using GAPDH as a reference.

FIG. 5. Immunofluorescence staining of day 7 differentiated hMGSCs and teratoma analysis. Attached EBs were assessed for protein expression as shown in (A): VWF. (B): VWF with DAPl overlay. (C): ACTC. (D): ACTC with DAPl overlay. (E): NES. (F): NES with DAPl overlay. Scale bars represent 50 pm. (G): Analysis of teratomas 8 weeks post-transplantation. Shown is a representative section of the NK7 cell graft after 8 weeks of in vivo differentiation. (H): Expression analysis of the human SRY gene was performed using genomic DNA isolated from a NK7 paraffin embedded tissue slide (lane I), NK7 genomic DNA (lane 2), sperm genomic DNA (lane 3) and female mouse genomic DNA (lane 4) as template. Shown are PCR products separated by gel electrophoreses. The fragment amplified with the SRY primers has a size of 350 base pairs.

FIG. 6. Immunofluorescence staining after 6 weeks of induced neural differentiation. hMGSCs were cultured on MEFs in hESC media (A) and were plated onto gelatin (B) prior to the differentiation experiment. Cells were stained for NES (C) before the treatment and following induced differentiation (D). Differentiated cells were also stained for the ectodermal markers MAP2 (E) and TUB I11 (F). Scale bars represent 50 pm.

Figure 7A:
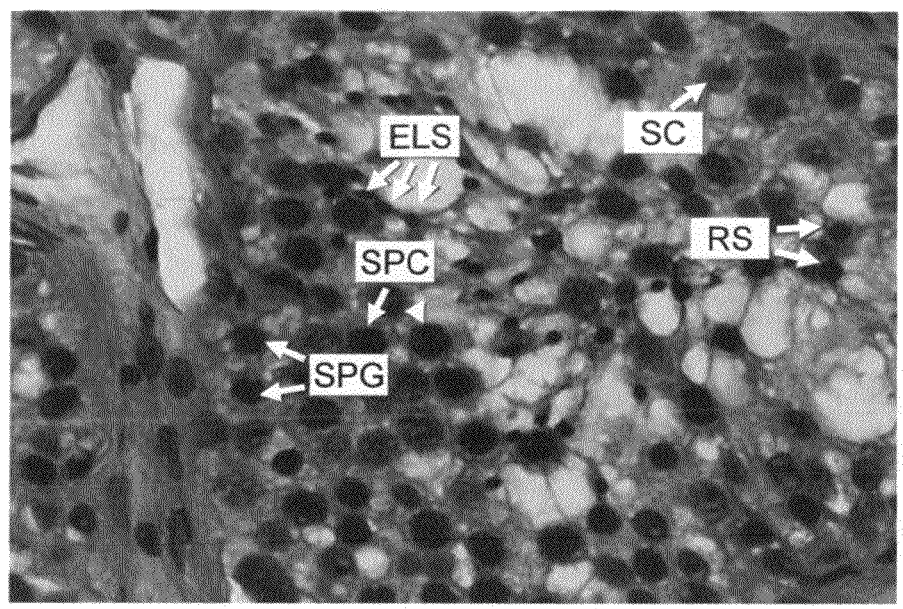
FIG. 7 illustrates the supplemental data in the present specification.
Figure 7B:
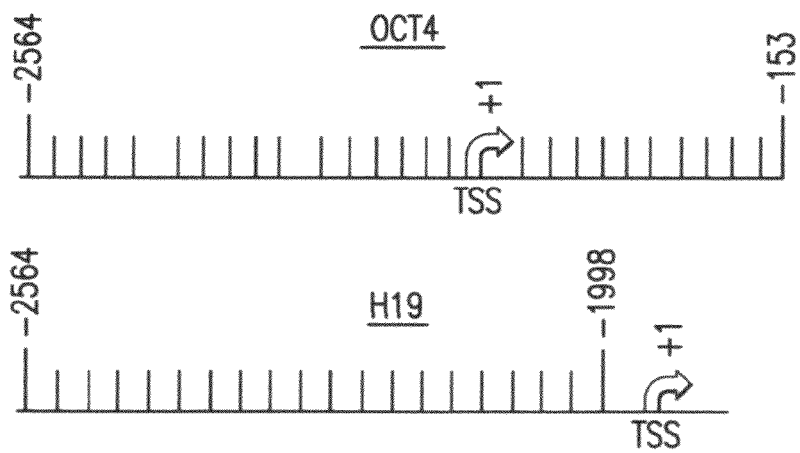
Figure 7C:
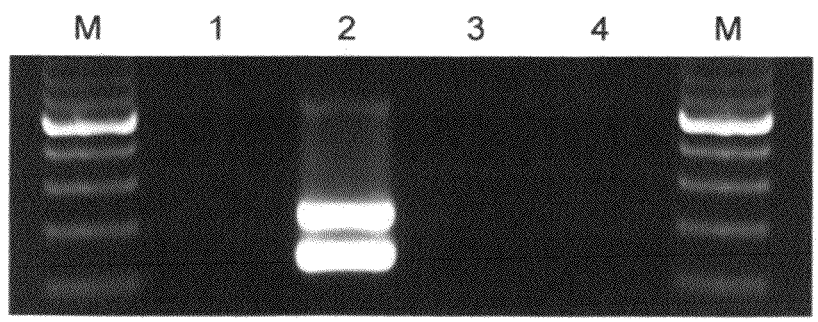

Supplemental Data is depicted in FIG. 7.

(A): Histological data showing normal spermatogenesis of the testicular tissue sample donor. Arrows indicate spermatogonial stem cells (SPGs), spermatocytes (SPCs), round spermatids (RS), elongating spermatids (ELS) and Sertoli Cells (SC).

(B): Schematic overview of the primer localization within the OCT4 promoter region and the DMR upstream of the HI9 promoter. The region analyzed in this study extends from nucleotide position $-2564$ bp to $+153$ bp of the OCT4 promoter and from $-2226$ to position $-1988$ of the DMR of the HI9 gene. TSS indicates the transcription start site of the gene. (C): Specificity of HI9 primers was analyzed. Genomic DNA was isolated from MEFs (lane 1) and human blood (2) and was subsequently converted. Shown are RT-PCR products separated by gel electrophoresis. While distinct bands can be determined in the human blood sample (2), no band could be detected in lane 1 or lane 3 and 4 which show the negative controls for both PCRs. Table 1. Variable number of tandem repeat (VNTR)I short tandem repeat (STR) analysis of 15 STR loci. Samples analyzed were genomic DNA isolated from NK7 hMGSCs, the tissue donor's blood sample and genomic DNA from H9 hESCs. The name of each STR locus and the corresponding number of short tandem repeats for both alleles are listed, FIG. 8 illustrates isolation of spermatogonial stem cells (SSCs). Enzymatic digestion of testicular tissue is followed by co-culture of the digestion product with Sertoli cells (shown in A), or MACS is used to produce an enriched fraction which is then co-cultured with Sertoli cells.

FIG. 9 illustrates a transwell insert culture wherein Sertoli cells are cultured on an extracellular mat which, itself, rests on a semi-permeable membrane.

FIG. 10 illustrates a hollow-fiber capillary culture. A) depicts a housing containing both hollow-fiber capillaries and extracapillary space with both ingress and egress portals. B) depicts a cross-section of a hollow-fiber capillary which contains in the intracapillary space an extra cellular matrix protein having thereon a monolayer of human Sertoli cells.

FIG. 11 illustrates various markers expressed during human spermatogenesis. The acronyms used: SSC, SPG, SPT and SPZ are defined in the figure.

What is claimed:

1. A method of obtaining human multipotent germ line stem cells, comprising the steps of:
    a) co-culturing spermatogonia and somatic cells isolated from human testicular tissue with feeder cells in a medium to form testicular cell colonies,
    b) co-culturing one or more testicular cell colonies on feeder cells in a medium, the testicular cell colonies comprising spermatogonial cells, and
    c) selecting one or more human multipotent germ line cells expressing a germ line marker and a pluripotency marker from a colony of step b.

2. The method of claim 1, wherein the feeder cells are human Sertoli cells.

3. The method of claim 1, wherein said culturing is effected in an artificial biological environment.

4. The method of claim 3, wherein the artificial biological environment is a transwell insert culture.

5. The method of claim 3, wherein the artificial biological environment is a hollow-fiber capillary culture.

6. The method of claim 1, comprising the further step of:
    prior to step a), obtaining the human testicular tissue from a testis section of a human, wherein the human is an individual presenting with histologically normal spermatogenesis in the testis section.

7. The method of claim 1, wherein the individual presents with obstructive azoospermia.

8. The method of claim 7, wherein the patient is obstructive azoospermic due to acquired reproductive tract obstruction.

9. The method of claim 8, wherein the acquired reproductive tract obstruction is from trauma.

10. The method of claim 1, wherein the feeder cell medium includes feeder cell layers under hESC conditions.

11. The method of claim 1, wherein the germ line marker is DAZL and the pluripotency marker is STELLAR.

12. A cell or cells obtained by the method of claim 1, said cell or cells expressing markers comprising DAZL, a germ line marker, and STELLAR, a pluripotency marker.

13. The cell or cells of claim 12, which is or are karotypically normal.

14. The cell or cells of claim 12, which expresses or express telomerase.

15. The cell or cells of claim 12, which expresses or express alkaline phosphatase.

16. A method of in vitro maturation of human germ line stem cells to haploid germ cells, which comprises the steps of:
   a) isolating human spermatogonial stem cells (SSCs) expressing a germ line marker and a pluripotency marker from a human presenting with histologically normal spermatogenesis, and optionally purifying the same;
   b) co-culturing the isolated and optionally purified SSCs with human Sertoli cells in a medium comprising gonadotropins, and
   c) identifying haploid germ cells.

17. The method of claim 16, wherein the co-culturing is effected in an in vitro device.

18. The method of claim 17, wherein the in vitro device is a transwell insert culture.

19. The method of claim 17, wherein the in vitro device is a hollow-fiber capillary culture.

20. The method of claim 16, comprising the further step of:
   prior to step a), selecting as the human, an individual presenting with histologically normal spermatogenesis.

21. The method of claim 16, wherein the individual presents with obstructive azoospermia.

22. The method of claim 21, wherein the individual presents with obstructive azoospermia due to acquired reproductive tract obstruction.

23. The method of claim 22, wherein the acquired reproductive tract obstruction is from trauma.

24. The method of claim 16, comprising the further step of:
   prior to step a), selecting as SSCs, cells which express markers comprising a germ line marker and a pluripotency marker.

25. The method of claim 16, wherein the germ line marker is DAZL and the pluripotency marker is STELLAR.

26. The method of claim 16, wherein the gonadotropins comprise one or more from the group consisting of FSH, LH and testosterone.

27. A method of producing human haploid germ cells in vitro, which comprises the steps of:
   a) isolating human spermatogonial stem cells (SSCs) expressing a germ line marker and a pluripotency marker from a human presenting with histologically normal spermatogenesis, and optionally purifying the same;
   b) co-culturing the isolated and optionally purified SSCs with Sertoli cells in an isolated and artificial biological environment in a medium comprising gonadotropins to obtain haploid germ cells; and
   c) detecting the presence of primary and secondary spermatocytes with spermatocyte specific markers and ploidy analysis as the SSCs of step b) differentiate.

28. The method of claim 27, comprising the further step of:
   prior to step a), selecting as the human, an individual presenting with histologically normal spermatogenesis.

29. The method of claim 27, wherein the individual presents with obstructive azoospermia.

30. The method of claim 29, wherein the individual presents with obstructive azoospermia due to acquired reproductive tract obstruction.

31. The method of claim 30, wherein the acquired reproductive tract obstruction is from trauma.

32. The method of claim 27, comprising the further step of:
   prior to step a), selecting as the human spermatogonial stem cells (SSCs), cells which express markers comprising a germ line marker and a pluripotency marker.

33. The method of claim 32, wherein the germ line marker is DAZL and the pluripotency marker is STELLAR.

34. The method of claim 27, wherein the gonadotropins comprise one or more from the group consisting of FSH, LH and testosterone.

* * * * *